(12) United States Patent
Appendino et al.

(10) Patent No.: US 9,802,880 B2
(45) Date of Patent: Oct. 31, 2017

(54) CANNABIGEROL DERIVATIVES

(71) Applicant: VIVACELL BIOTECHNOLOGY ESPAÑA S.L., Córdoba (ES)

(72) Inventors: Giovanni Appendino, Turin (IT); María Luz Bellido Cabello De Alba, Córdoba (ES); Eduardo Muñoz Blanco, Córdoba (ES)

( * ) Notice: Subject to any disclaimer, the term of this patent is extended or adjusted under 35 U.S.C. 154(b) by 0 days.

(21) Appl. No.: 15/122,160

(22) PCT Filed: Feb. 12, 2015

(86) PCT No.: PCT/EP2015/053032
§ 371 (c)(1),
(2) Date: Aug. 26, 2016

(87) PCT Pub. No.: WO2015/128200
PCT Pub. Date: Sep. 3, 2015

(65) Prior Publication Data
US 2017/0247308 A1    Aug. 31, 2017

(30) Foreign Application Priority Data
Feb. 27, 2014  (EP) .................................. 14156954

(51) Int. Cl.
| C07C 50/28 | (2006.01) |
| A61K 31/122 | (2006.01) |
| A61K 31/13 | (2006.01) |
| A61K 31/215 | (2006.01) |
| C07C 69/757 | (2006.01) |
| C07C 225/28 | (2006.01) |

(52) U.S. Cl.
CPC ............ *C07C 50/28* (2013.01); *A61K 31/122* (2013.01); *A61K 31/13* (2013.01); *A61K 31/215* (2013.01); *C07C 69/757* (2013.01); *C07C 225/28* (2013.01); *C07C 2601/14* (2017.05)

(58) Field of Classification Search
None
See application file for complete search history.

(56) References Cited

FOREIGN PATENT DOCUMENTS

| EP | 2551255 A1 | 1/2013 |
| WO | 2011117429 A1 | 9/2011 |

OTHER PUBLICATIONS

Ahmadian, M.; Suh, J.M.; Hah, N.; Liddle, C.; Atkins, A.R.; Downes, M.; Evans, R.M.; "PPARy signaling and metabolism: the good, the bad and the future", Nat Med., (2013), vol. 19, pp. 557-566.

Barish GD; Narkar VA; Evans RM, "PPAR6: a dagger in the heart of the metabolic syndrome", J Clin Invest., (2006), vol. 116, pp. 590-597.
Bernardo A; Minghetti L, "Regulation of Glial Cell Functions by PPAR- gamma natural and Synthetic Agonists", PPAR RES., (2008), p. 864140.
Bolton JL; Trush MA; Penning TM; Dryhurst G; Monks TJ, "Role of quinones in toxicology", Chem Res Toxicol., (2000), vol. 3, pp. 135-160.
Burstein S, "PPAR-gamma: a nuclear receptor with affinity for cannabinoids", Life Sci, (2005), vol. 77, pp. 1674-1684.
Ciudin A; Hernandez C; SIM6 R, "Update on cardiovascular safety of PPARgamma agonists and relevance to medicinal chemistry and clinical pharmacology", Curr Top Med Chem., (2012), vol. 12, pp. 585-604.
Doshi LS; Brahma MK; Bahirat UA; Dixit AV; Nemmani KV, "Discovery and development of selective PPAR gamma modulators as safe and effective antidiabetic agents", Expert Opin Investig Drugs, (2012), vol. 19, pp. 489-512.
Ferguson H.E.; Kulkarni A.; Lehmann G.M.; Garcia-Bates T.M.; Thatcher T.H.; Huxlin K.R. et al.; "Electrophilic peroxisome proliferator-activated receptor-gamma ligands have potent antifibrotic effects in human lung fibroblasts", Am J Respir Cell Mol Biol., (2009), vol. 41, pp. 722-730.
Fievet C; Fruchart J.C.; Staels B.; "PPAR alpha and PPAR gamma dual agonists for the treatment oftype2 diabetes and the metabolicsyndrome", Curr. Opin. Pharmacol., (2006), vol. 6, pp. 606-614.
Gelman, L.; Feige, J.N.; Desvergne, B., "Molecular basis of selective PPARgamma modulation for the treatment of type 2 diabetes", Biochim. Biophys.Acta, (2007), vol. 1771, No. 8, pp. 1094-1107.
Ghoochani A; Shabani K; Peymani M; Ghaedi K; Karamali F; Karbalaei K; Tanhaie S; Salamian A; Esmaeili A; Valian-Borujeni S, "The influence of peroxisome proliferator-activated receptor g(1) during differentiation of mouse embryonic stem cells to neural cells", Differentiation, (2012), vol. 83, pp. 60-67.

(Continued)

*Primary Examiner* — Michael Barker
(74) *Attorney, Agent, or Firm* — Moore Patents; David Dreyfuss

(57) ABSTRACT

The present invention relates to novel cannabigerol quinone derivatives of formula (I) wherein R is the carbon atom of a linear or branched group, represented by: aryl, alkenyl, alkynyl or alcoxycarbonil groups; or wherein R is the nitrogen atom of a linear or branched group, represented by: alkylamino, arylamino, alkenylamino or alkynylamino groups; or, alternatively, R represents a bond between 2 molecules of formula (I) forming a dimer. The invention also relates to the use of any of the compounds of formula (I) as medicaments in therapy, particularly for treating PPARg-related diseases due to their high PPARg agonistic effect lacking electrophilic (Nrf2 activation) and cytotoxic activities. This invention also provides pharmaceutical compositions comprising said compounds and method of treating diseases with said compounds.

(I)

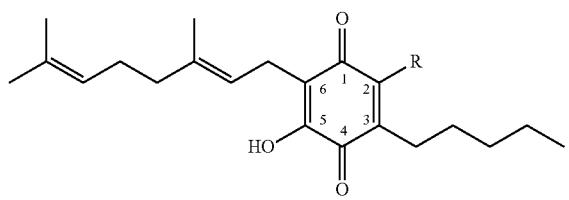

18 Claims, 21 Drawing Sheets

(56) References Cited

OTHER PUBLICATIONS

Granja AG; Carrillo-Salinas F; Pagani A; Gomez-Canas M; Negri R; Navarrete C; Mecha M; Mestre L; Fiebich BL; Cantarero I, "A cannabigerol quinone alleviates neuroinflammation in a chronic model of multiple sclerosis", J Neuroimmune Pharmacol., (2012), vol. 4, pp. 1002-1016.

Itoh T; Fairall L; Amin K; Inaba Y; Szanto A; Balint BL; Nagy L; Yamamoto K; Schwabe JW, "Structural basis for the activation of PPARgamma by oxidized fatty acids", Nat Struct Mol Biol, (2008), vol. 15, pp. 924-931.

Kogan NM; Rabinowitz R; Levi P; Gibson D; Sandor P; Schlesinger M; Mechoulam R, "Synthesis and antitumor activity of quinonoid derivatives of cannabinoids", J Med Chem, (2004), vol. 47, pp. 3800-3806.

Lehmann JM; Moore LB; Smith-Oliver TA; Wilkison WO; Willson TM; Kliewer SA, "An antidiabetic thiazolidinedione is a high affinity ligand for peroxisome proliferator-activated receptor gamma (PPAR gamma)", J Biol Chem., (1995), vol. 270, pp. 12953-12956.

Li Y; Zhang J; Schopfer FJ; Martynowski D; Garcia-Barrio MT; Kovach A; Suino-Powell K; Baker PR; Freeman BA; Chen YE, "Molecular recognition of nitrated fatty acids by PPAR gamma", Nat Struct Mol Biol, (2008), vol. 15, pp. 865-867.

Liberato MV; Nascimento AS; Ayers SD; Lin JZ; Cvoro A; Silveira RL; Martinez L; Souza PC; Saidemberg D; Deng T, "Medium Chain Fatty Acids are Selective Peroxisome Proliferator activated Receptor (PPAR) c Activators and Pan-PPAR Partial Agonists", PLOS One, (2012), vol. 7, p. E36297.

Liu J; Li H; Burstein SH; Zurier RB; Chen JD, "Activation and binding of peroxisome proliferator-activated receptor gamma by synthetic cannabinoid ajulemic acid", Mol. Pharmacol., (2003), vol. 63, pp. 983-992.

Monks TJ; Jones DC, "The metabolism and toxicity of quinones, quinonimines, quinone methides, and quinone-thioethers", Curr Drug Metab., (2002), vol. 4, pp. 425-438.

Morales P; Vara D; Gomez-Canas M; Zuniga MC; Olea-Azar C; Goya P; Fernandez-Ruiz J; Diaz-Laviada I; Jagerovic N, "Synthetic cannabinoid quinones: preparation, in vitro antiproliferative effects and in vivo prostate antitumor activity", Eur J Med Chem., (2013), vol. 70, pp. 111-119.

NA HK; Surh YJ, "Oncogenic potential of Nrf2 and its principal target protein heme oxygenase-1", Free Radic Biol Med., (2013), vol. 67, pp. 353-365.

Nolte RT; Wisely GB; Westin S; Cobb JE; Lambert MH; Kurokawa R; Rosenfeld MG; Willson TM; Glass CK; Milburn MV, "Ligand binding and co-activator assembly of the peroxisome proliferator-activated receptor-gamma", NATURE, (1998), vol. 395, pp. 137-143.

O'Sullivan SE, "Cannabinoids go nuclear: evidence for activation of peroxisome proliferator-activated receptors", BR J Pharmacol., (2007), vol. 152, pp. 576-582.

Poulsen L; Siersbaek M; Mandrup S, "PPARs: fatty acid sensors controlling metabolism", Semin Cell Dev Biol., (2012), vol. 23, pp. 631-639.

Rosen ED; MacDougald OA, "Adipocyte differentiation from the inside out", Nat Rev Mol Cell Biol., (2006), vol. 7, pp. 885-896.

Solis L. M.; Behrens C.; Dong W.; Suraokar M.; Ozburn N. C.; Moran C. A.; Corvalan A. H.; Biswal S.; Swisher S. G.; Bekele B. N.; "Nrf2 and Keap1 abnormalities in non-small cell lung carcinoma and association with clinicopathologic features", Clin Cancer Res., (2010), vol. 16, pp. 3743-3753.

Sporn, M. B.; Liby, K. T.; "NRF2 and cancer: the good, the bad and the importance of context", Nat. Rev. Cancer, (2012), vol. 12, pp. 564-557.

Stienstra R; Duval C; Muller M; Kersten S, "PPARs, obesity, and inflammation", PPAR Res., (2007), p. 95974.

Sun Y; Bennett A, "Cannabinoids: A New Group of Agonists of PPARs", PPAR Res., (2007), p. 23513.

Széles, L; Torocsik, D.; Nagy, L., "PPARgamma in immunity and inflammation: cell types and diseases", Biochim. Biophys. Acta, (2007), vol. 1771, pp. 1014-1030.

Tachibana K; Yamasaki D; Ishimoto K; Doi T, "The Role of PPARs in Cancer", PPAR Res., (2008), p. 102737.

Tontonoz P; Spiegelman BM, "Fat and beyond: the diverse biology of PPARgamma", Annu Rev Biochem., (2008), vol. 77, pp. 289-312.

Vanden Berghe W; Vermeulen L; Delerive P; Debosscher K; Staels B; Haegeman G, "A paradigm for Jene regulation: inflammation, NF-kB and PPAR", Adv.Exp.Med.Biol., (2003), vol. 544, pp. 181-196.

Wang W; Liu F; Chen N, "Peroxisome proliferator-activated receptor-gamma (PPAR-gamma) agonists attenuate the profibrotic response induced by TGF-beta1 in renal interstitial fibroblasts", Mediators Inflamm, (2007), p. 62641.

Zhao C; Chen W; Yang L; Chen L; Stimpson SA; Diehl AM, "PPARgamma agonists prevent TGFbeta1/Smad3-signaling in human hepatic stellate cells", Biochem Biophys Res Commun., (2006), vol. 350, pp. 385-391.

Zhang GY; Yi CG; Li X; Ma B; Li ZJ; Chen XL; Guo SZ; Gao WY, "Troglitazone suppresses transforming growth factor-beta1-induced collagen type I expression in keloid fibroblasts", Br J Dermatol., (2009), vol. 160, pp. 762-770.

Figure 4
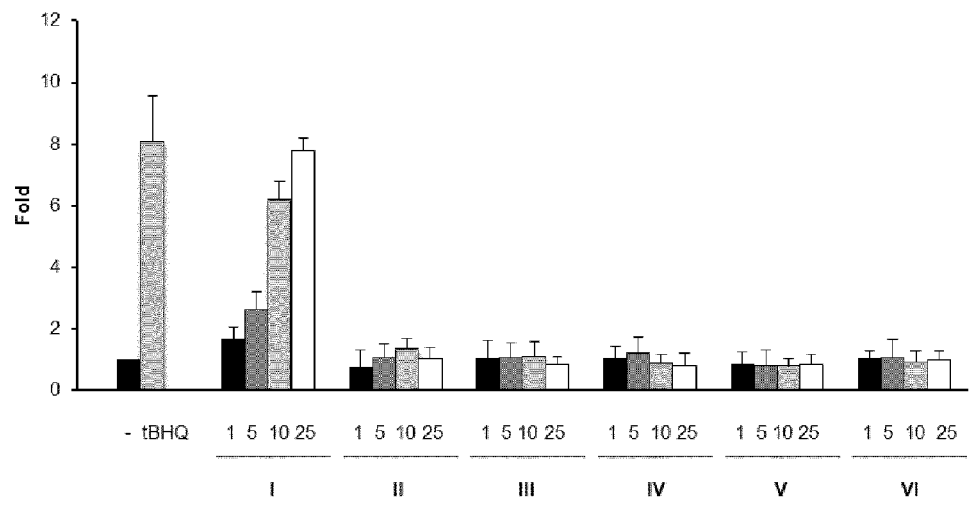
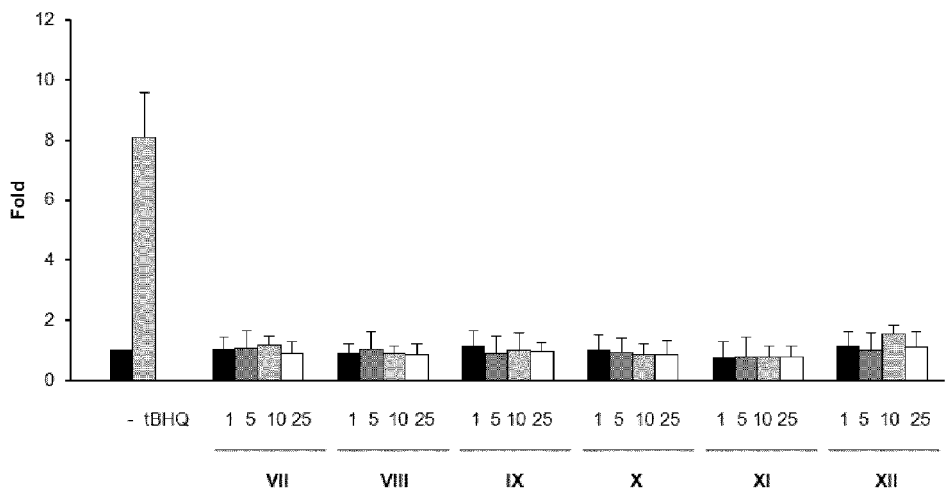

Figure 10
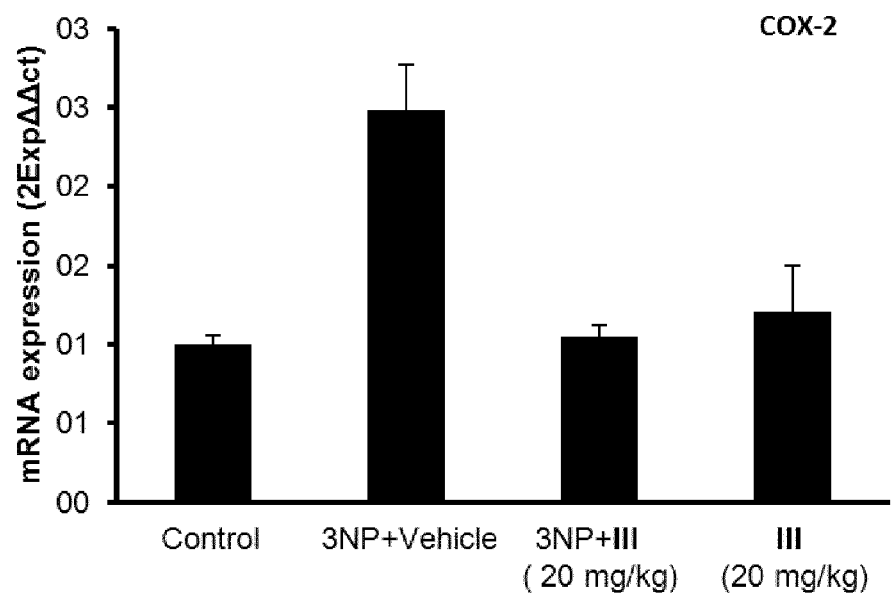
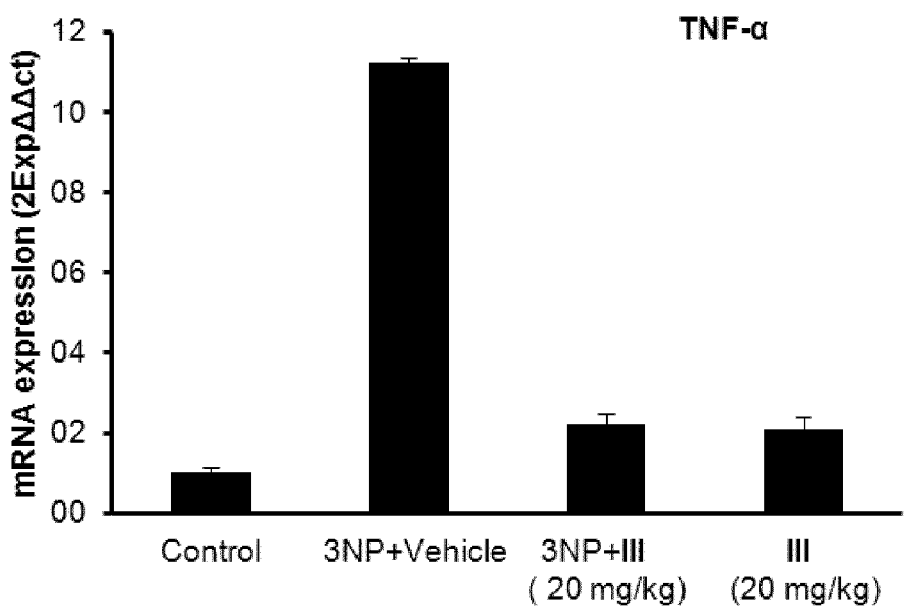

Figure 10 (cont.)
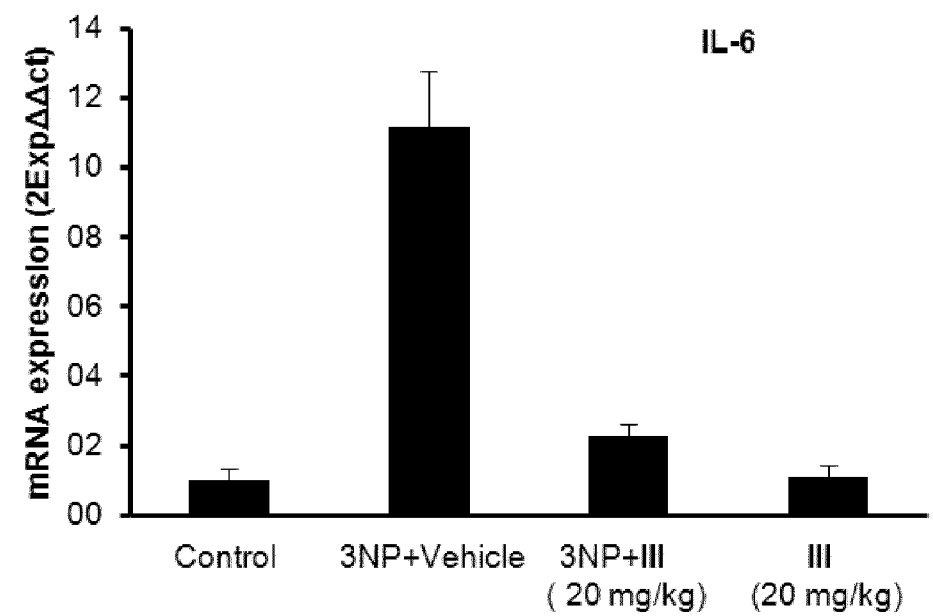
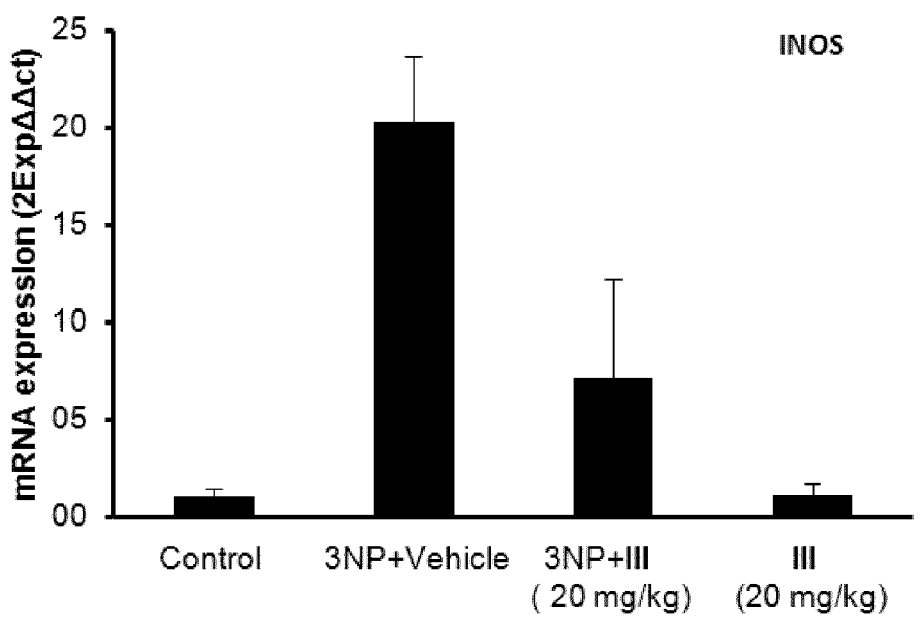

Figure 11 (cont.)
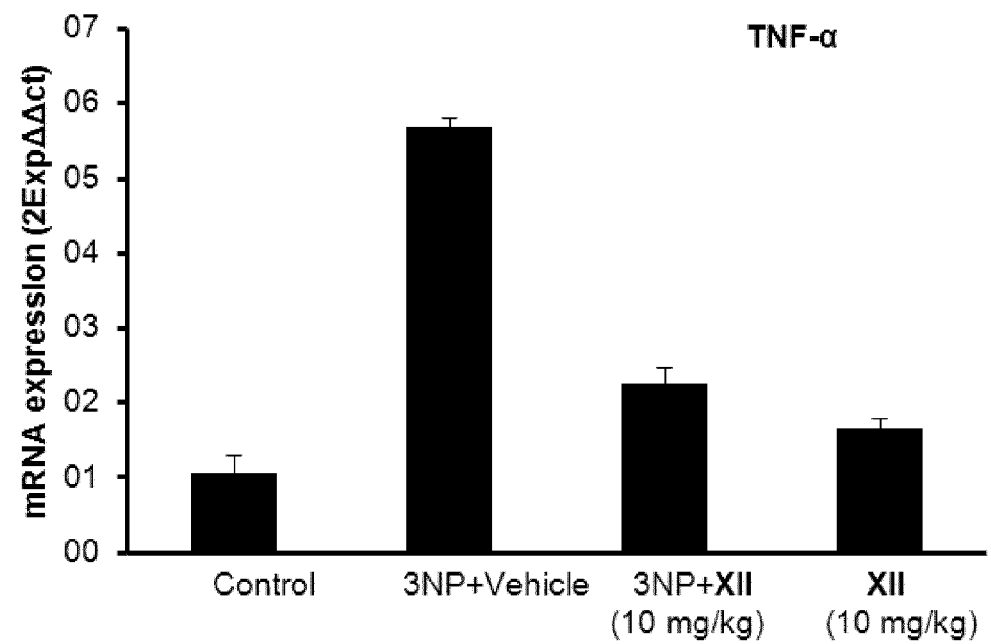
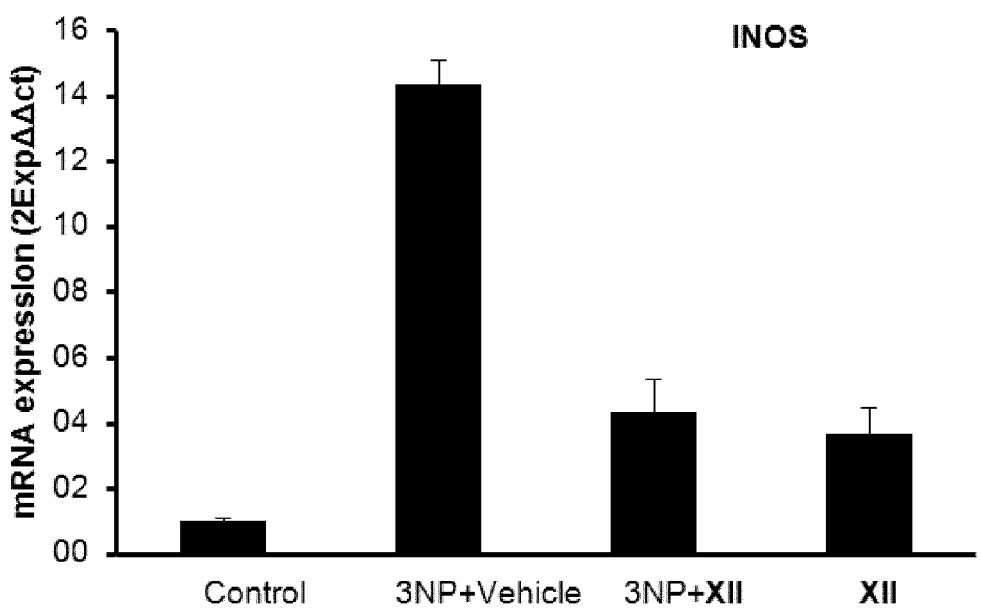

Figure 12
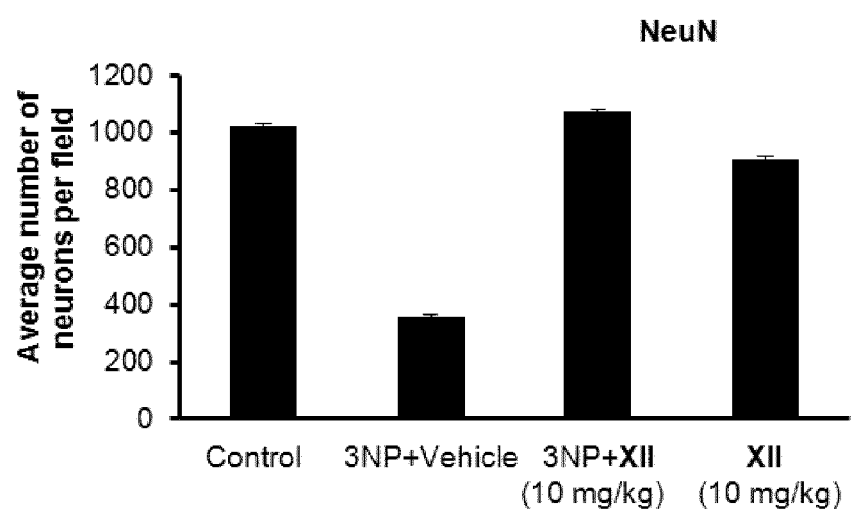
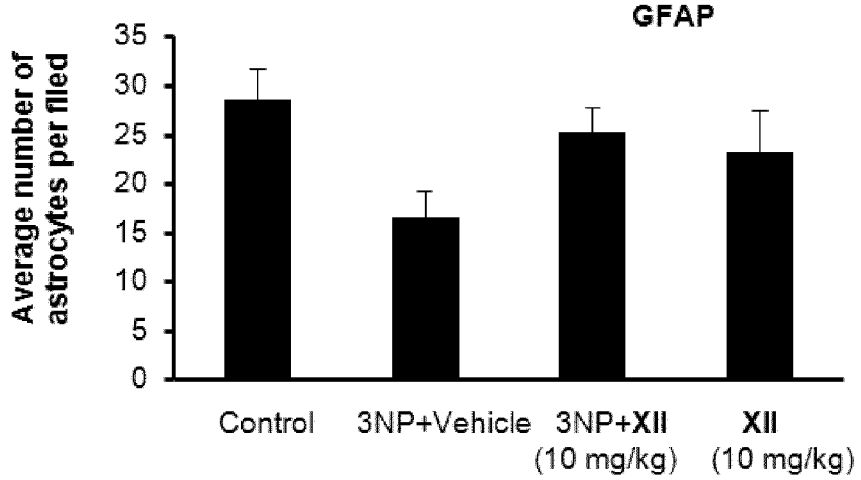

Figure 13
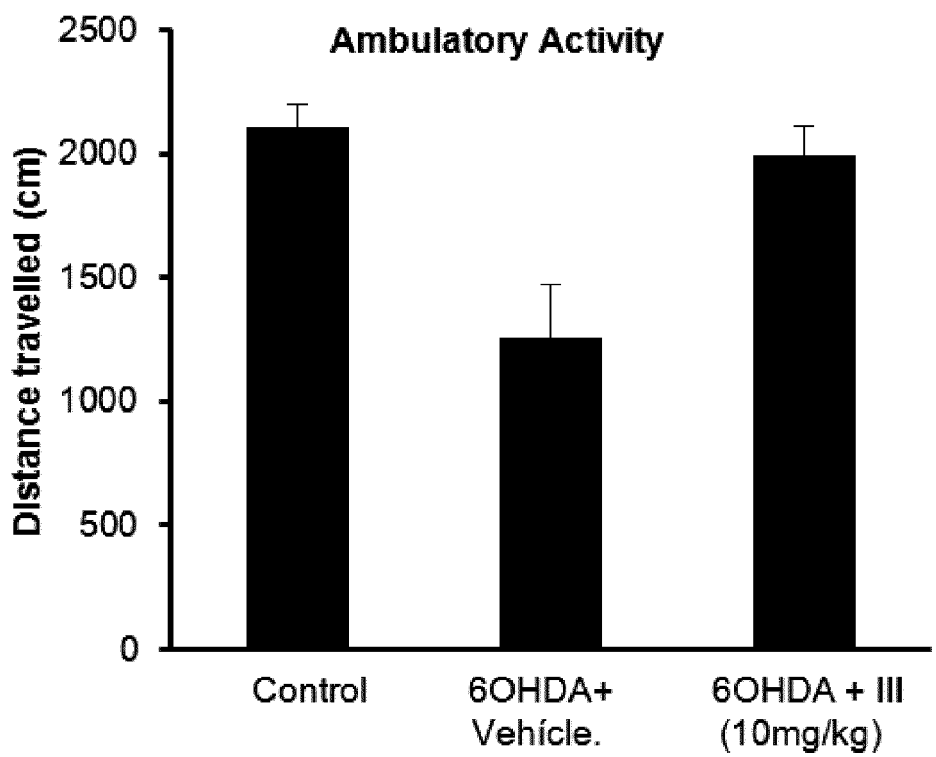
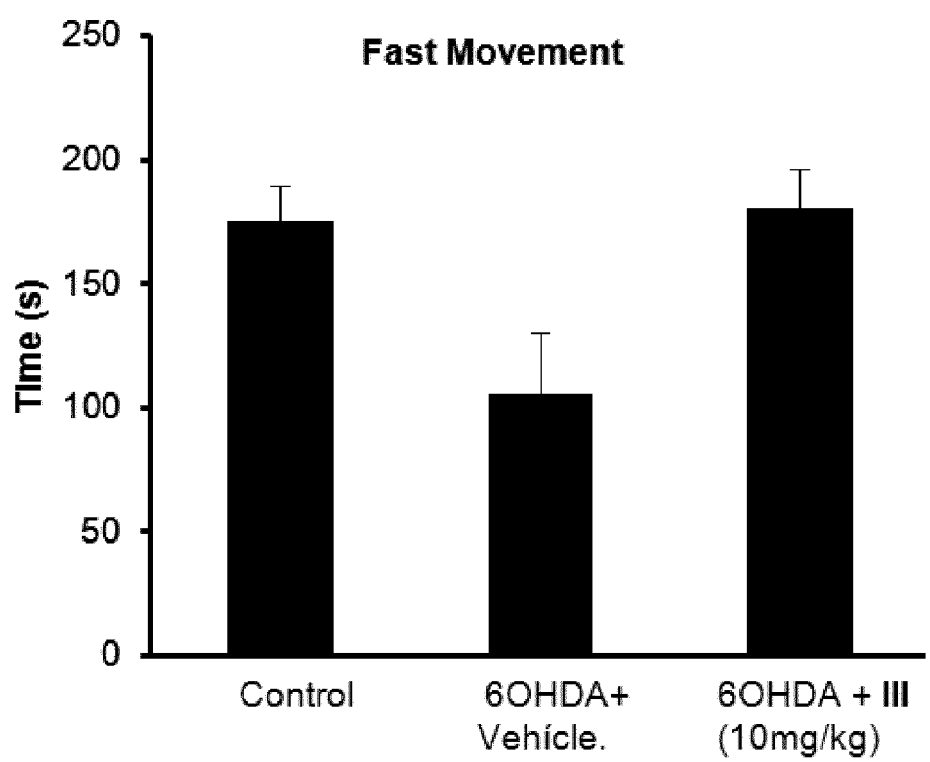

CANNABIGEROL DERIVATIVES

FIELD OF THE INVENTION

The present invention relates to novel cannabigerol quinone derivatives, and the synthesis of those compounds. Furthermore, the present invention relates to their use as a medicament and in therapy, particularly as peroxisome proliferator-activated receptor gamma (PPARg) modulators, for treating diseases and conditions responsive to PPARg modulation. This invention also provides pharmaceutical compositions comprising said compounds and method of treating diseases with said compounds.

BACKGROUND OF THE INVENTION

Nuclear receptors (NRs) are a major target of drug discovery. NRs are ligand-dependent transcription factors that possess the ability to directly interact with DNA regulating the transcriptional activity of their target genes. These receptors play essential roles in development, cellular homeostasis and metabolism. Moreover, NRs have been implicated in a wide range of diseases and, as such, have been the focus of drug development efforts for the pharmaceutical industry.

In the newest nomenclature for nuclear receptors, Perixome Proliferator Activated Receptors (PPARs), Nuclear subfamily 1 C (NR1C) comprises three subtypes of mammals PPARs: PPARα (also called NR1C1), PPARβ/δ (also called NR1C2) and PPARγ (also called PPARg, glitazone receptor or NR1C3).

PPARs control the expression of networks of genes involved in adipogenesis, lipid metabolism, inflammation and maintenance of metabolic homeostasis [Barish et al., 2006]. Those nuclear receptors activate transcription by binding to elements of DNA sequences, known as peroxisome proliferator response elements (PPRE), in the form of a heterodimer with retinoid X receptors (known as RXRs).

Similar to typical nuclear receptors, PPARs are comprised of distinct functional domains, including an N-terminal transactivation domain (AF1), a highly conserved DNA-binding domain (DBD) and a C-terminal ligand-binding domain (LBD) containing a ligand-dependent transactivation function (AF2) [Poulsen et al., 2012]. The DNA-binding C domain, composed of two zinc fingers, binds to the peroxisome proliferator response element (PPRE) in the regulatory region of PPAR target genes.

PPARs negatively regulate the transcription of inflammatory response genes by antagonizing the Activator Protein-1 (AP-1), Nuclear Factor-kappa B (NF-kB), signal transducer and activator of transcription 3 (STAT3) and Nuclear Factor of Activated T-cells (NFAT) signaling pathways [Vanden Berghe et al. 2003].

Peroxisome Proliferator-activated Receptor gamma (PPARg) is of special interest because it is involved in the regulation of adipocyte formation, insulin sensitivity and inflammation [Fievet et al. 2006] [Stienstra et al. 2007] [Tontonoz and Spiegelman, 2008]. This nuclear receptor is expressed in a range of tissues including adipose tissue, skeletal muscle cells, osteoclasts, osteoblasts, several immune-type cells, and in the brain and peripheral nervous system.

It is clear that PPARg is the dominant or "master" regulator of adipogenesis, due to the fact that is both sufficient and necessary for fat cell differentiation. The regulatory regions of a large number of genes that play important roles in lipogenesis and insulin sensitivity contain binding sites for PPARg, including aP2, LPL, adiponectin, and Glut4 [Rosen and MacDougald, 2006]. Therefore, activation of PPARg in adipose tissue impacts whole-body insulin sensitivity.

On the other hand, activation of PPARg exerts anti-inflammatory activities in several cell types by inhibiting the expression of pro-inflammatory genes, thereby reducing the production of cytokines, metalloproteases and acute-phase proteins [Tontonoz and Spiegelman, 2008]. It also acts increasing anti-inflammatory cytokines, and inhibiting inducible nitric oxide synthase (iNOS) expression [Széles et al., 2007].

PPARg has been recognized as playing a fundamentally important role in the immune response through its ability to direct the differentiation of immune cells towards anti-inflammatory phenotypes [Tontonoz and Spiegelman, 2008]. Interestingly, PPARg agonists have shown anti-inflammatory and neuroprotective effects in several experimental models of Parkinson's diseases, amyotrophic lateral sclerosis, multiple sclerosis and stroke, as well as in a few clinical studies [Bernardo and Minghetti, 2008]. Additionally, PPARg must formally be considered a tumor suppressor gene in the genetic sense. It is expressed in a variety of tumor cells, and the activation of PPARg by ligands led to either inhibition of cell proliferation or induction of apoptosis [Tachibana et al., 2008] [Tontonoz and Spiegelman, 2008].

The beneficial effects of PPARg activation can be used for the treatment of several PPARg mediated diseases, as is shown in Table 1. For the purposes of present description PPARg mediated disease means any pathological effect observed which might be due to the alteration of PPARg function in normal non-pathological conditions. This table summarizes the actions of PPARs in inflammatory, cancer diseases and other diseases.

TABLE 1

| Disease | Effect of PPARγ and its ligands |
|---|---|
| Atherosclerosis | ↓Recruitment of immune cells. |
| | ↓Migration and proliferation of VSMC. |
| Inflammatory bowel diseases | ↓IL-β-induced IL-8 and MCP-1 in colonic epithelial cells. Modulation of inflammatory response: ↓Th1 and ↑Th2. Improvement of colitis in mice models. Improvement of colitis in 4/15 patients. |
| Rheumatoid arthritis | ↑Synoviocyte and chrondrocyte apoptosis. ↓TNFα, IL-1β and COX-2 in rheumatoid synoviocytes. Improvement of arthritis in mouse models |
| Liver fibrosis | ↓HSC activation. ↓Kupffer cell activation. |
| Nephropathy | ↓IL-1β, MCP-1, COX-2, iNOS, proliferation and ↑apoptosis in mesangial cells. Improvement of micro-albuminuria in Type II diabetic patients and diabetic rats. |
| Psoriasis and skin wound healing | Improvement of psoriatic lesions in mouse models and patients. |
| Scleroderma (SSc) | ↓Collagen production ↓Fibroblast proliferation and differentiation Interaction with Wnt pathway |
| Neuro-degenerative disorders | ↓iNOS, TNFα, IL-1β, IL-6, INFγ, MCP-1 and COX-2 in astrocytes and microglia. ↓Neuronal apoptosis. ↑Differentiation of neural stem cells |
| Cancer | ↑Apoptosis and ↓proliferation of cancer cells. ↓Colitis-related colon cancer in mouse models. |

Abbreviations: ↓ inhibition, ↑ stimulation, hepatic stellate cells (HSC), vascular smooth muscle cells (VSMC), monocyte chemoattractant protein-1 (MCP-1), T-helper (Th), tumor necrosis factor-α (TNFα), cyclooxygenase (COX), interferon-gamma (INFγ), inducible nitric oxide synthase (iNOS), intracellular adhesion molecule-1 (ICAM-1) [Adapted from Kostadinova et al., 2005].

Nuclear factor (erythroid-derived 2)-like 2, also known as NFE2L2 or (Nrf2), is a transcription factor that in humans is encoded by the NFE2L2 gene. The Nrf2 antioxidant response pathway is the primary cellular defense against the cytotoxic effects of oxidative stress. Among other effects, Nrf2 increases the expression of several antioxidant enzymes.

The Keap1-Nrf2 pathway is the major regulator of cytoprotective responses to endogenous and exogenous stresses caused by reactive oxygen species (ROS) and electrophiles. The key signaling proteins within the pathway are the transcription factor Nrf2 that binds together with small Maf proteins to the antioxidant response element (ARE) in the regulatory regions of target genes. Under the basal condition, Nrf2-dependent transcription is repressed by a negative regulador, Keap1 (Kelch ECH associating protein 1). When cells are exposed to oxidative stress, electrophiles, or chemopreventive agents, Nrf2 escapes Keap1-mediated repression and activates antioxidant responsive element (ARE)-dependent gene expression to maintain cellular redox homeostasis.

Since this Nrf2-dependent cellular defense response is able to protect multi-organs or multi-tissues, activation of Nrf2 has been implicated in conferring protection against many human diseases, including cancer, neurodegenerative diseases, cardiovascular diseases, acute and chronic lung injury, autoimmune diseases, and inflammation Nrf2 can protect cells and tissues from a variety of toxicants and carcinogens by increasing the expression of a number of cytoprotective genes. Just as Nrf2 protects normal cells, studies have shown that Nrf2 may also protect cancer cells from chemotherapeutic agents and facilitate cancer progression [Na and Surh 2013].

Cancer cells survive persistent endogenous oxystress or reactive oxygen species (ROS)-induced cellular stress, and become resistant to certain anticancer agents that exert cytotoxicity through ROS production. Under such conditions, an active Nrf2 pathway could maintain a favorable redox balance in cancer cells by keeping ROS levels within a range that promotes their growth and survival. Sustained accumulation or activation of Nrf2 is speculated to confer on a subset of premalignant or cancerous cells an advantageous environment to proliferate, evade apoptosis, metastasize, and tolerate therapeutic intervention.

Inhibition of Nrf2 overexpression has been known to reverse the phenotypic characteristics of cancer cells, lending support to this supposition [Sporn and Liby, 2012]. Constitutive overactivation of Nrf2 has been observed in numerous types of malignancies, such as squamous cell carcinomas, lung cancer, breast cancer, gallbladder cancer, prostate cancer, renal cancer, ependymomas, ovarian epithelial carcinoma, endometrial cancer, and pancreatic cancer [Na and Surh, 2013]. Cancer patients with a constitutively elevated level of Nrf2 expression in their tumor, in general, show a lower survival rate [Solis et al., 2010]. Therefore, Nrf2 is considered a prognostic molecular marker for determining the status of cancer progression and contributes to both intrinsic and acquired chemoresistance. Thus, this antioxidant transcription factor may also act as a proto-oncogene and enhanced Nrf2 activity promotes formation and chemoresistance of solid cancers [Sporn and Liby, 2012].

CBG-Q (compound I), precursor of CBG-Q chemical derivatives (compounds II to XII) of present invention, exerts an activation effect on PPARg. However, CBG-Q also induces activation (see comparative example 4 and FIG. 4) of Nfr2, which provokes a non-desired side effect as tumors becoming resistant to chemotherapy agents, and a chronic treatment with Nrf2-activators may result in carcinogenesis, as explained above. Therefore, the new CBG derivatives of present invention, offer an alternative treatment for cancer more effective due that the side-effect of induced chemotherapy resistance, observed when CBG was administered in vitro, due to Nrf2 over-expression, is not present.

Among activators of PPARg ligands, the thiazolidindiones (TZDs) are of most clinical importance [Lehmann et al., 1995]. For this reason rosiglitazone and pioglitazone have been largely used so far in the clinical practice. They provide similar effects on glycemic control, as well as a range of similar adverse effects, such as weight gain, fluid retention, and increased risk of hearth failure, which seem to be PPARg mediated. Interestingly, those thiazolines differ on their effect on lipid and cardiovascular safety profile, indicating a PPARg-independent mechanism. Indeed, rosiglitazone was recently withdrawn in Europe and its use has been restricted in USA as a consequence of increased risk of cardiovascular events in type 2 diabetic patients.

Although TZDs are potent PPARg full agonists (PPARg-fa) their mechanism-based side effects have limited the full therapeutic potential of those compounds [Gelman et al., 2007] [Ciudin et al., 2012]. But the physiologic and therapeutic relevance of the PPARg pathway have promoted new studies to develop newer classes of molecules that reduce or eliminate adverse effects [Ahmadian et al., 2013]. Therefore, much progress has been achieved in the discovery and development of selective PPARg modulators (PPARg-m) as safer alternatives to PPARg-fa. The preclinical and clinical findings clearly suggest that selective PPARg-m have the potential to become the next generation of PPARg agonists: effective insulin sensitizers with a superior safety profile to that of PPARg-fa. [Doshi et al. 2010].

In this sense natural and synthetic cannabinoids are considered PPARg-m that alleviates inflammatory process through activation of PPARg. Some examples of cannabinoid-based PPARg-m are ajulemic acid [Liu et al., 2003], [Burstein S. 2005], WIN55212-2 [Sun and Bennett, 2007], $^9$Δ-THC and CBD [O'Sullivan 2007], and CBG and derivatives [Granja et al., 2012].

The clinical relevance of covalent modification of druggable proteins by small molecules has been extensively debated in the past few years by the pharmaceutical industry and some times covalent modification underlies the activity of successful drugs [Singh et al., 2011]. Nevertheless, there is still a rooted bias against covalent drugs irrespective of the mechanism by which they ultimately bind to biomolecules. Quinones represent a class of toxicological intermediates, which can create a variety of hazardous effects in vivo, including acute cytotoxicity and immunotoxicity [Bolton et al., 2000]. The mechanisms by which quinones cause these effects can be quite complex. Quinones are Michael acceptors, and cellular damage can occur through alkylation of crucial cellular proteins and/or DNA. Alternatively, quinones are highly redox active molecules which can redox cycle with their semiquinone radicals, leading to formation of reactive oxygen species (ROS) that can cause severe oxidative stress within cells through the formation of oxidized cellular macromolecules, including lipids, proteins, and DNA [Monks and Jones, 2012]. Although there are numerous examples of quinone-based compounds with therapeutic use the concerns over non-specific toxicity and lack of selectivity, the Michael acceptor motif is rarely introduced by design in drug leads.

One example of quinone-based therapeutic compounds is report in the patent WO2011117429 that describes the synthesis of cannabigerol hydroxy-quinone (also named CBG-Q or VCE-003 in the aforesaid international patent application and, for the purposes of present specification, also called compound I) and its use in diseases and conditions responsive to PPARg modulation. Diseases mentioned in WO/2011/117429 are: atherosclerosis, inflammatory bowel diseases, rheumatoid arthritis, liver fibrosis, nephropathy, psoriasis, skin wound healing, skin regeneration, pancreatitis, gastritis, neurodegenerative disorders, cancer; hypertension, hypertrigliceridemia, hypercholesterolemia, obesity and Type II diabetes. The introduction of a quinone motif in the cannabigerol molecule increases its affinity to bind PPARg and increases its transcriptional activity.

Further research shows that cannabigerol hydroxyquinone (CBG-Q or compound I) also activates the transcription factor Nrf2, a cellular sensor of oxidative/electrophilic stress. Thus, introduction of a quinone motif in cannabigerol results in two independent activities such as those exerted as PPARg agonists and Nrf2 activators.

To improve just PPARg agonistic activity, but without inducing activation of Nrf2, in order to avoid induction of resistance to chemotherapy, present invention has developed a library of novel compounds starting from Cannabigerol hydroxyquinone as a template and surprisingly we have found that specific modifications in position 2 resulted on novel compounds suitable for treating PPARg-related diseases due to their high PPARg agonistic effect lacking electrophilic (Nrf2 activation) and cytotoxic activities.

Those cannabigerol hydroxy-quinone derivatives of present invention are different from the compounds described in WO20011117429, since the modifications in position 2 confers to the compounds of the present invention the capacity to activate to PPARg and to protect from glutamate-induced cytotoxicity. These compounds also shown a remarkable low cytotoxicity in cell lines of neuronal origin compared with CBG-Q (compound I) comprised in the state of the art. In addition derivatives of this compounds show therapeutic efficacy in animal models of diseases (Multiple Sclerosis, Parkinson and Huntington diseases) widely used to evaluate the clinical efficacy of PPARg agonists.

SUMMARY OF THE INVENTION

Departing from the prior art, the problem of the present invention is to provide cannabigerol hydroxyl-quinone derivatives with exhibits activity in modulating PPARg without inducing activation of Nrf2.

The compounds of the invention also comprise their analogs, derivatives, tautomeric forms, isomers, stereoisomers, polymorphs, pharmaceutically acceptable salts, pharmaceutically acceptable solvates, and compositions containing the same.

For the purposes of present description the term "analogue/s" refers to any entity structurally derived or homologous to the compounds of formula (I).

In the context of this invention "derivative/s" of the compounds of formula (I) should be interpreted as any CBG-Q analogue, always substituted in position 2 and showing the pharmacological properties linked to that substitution in position 2, as defined herein, but also having moieties replacements in other positions of the CBG-Q molecule, different to the groups shown in said formula (I).

The term "tautomers" are constitutional isomers of organic compounds that readily interconvert by a chemical reaction (tautomerization).

The term "isomers" or "stereoisomers" refers to compounds, which have identical chemical constitution, but differ with regard to the arrangement of the atoms or groups in space.

As used herein "polymorph" refers to crystalline forms having the same chemical composition but different spatial arrangements of the molecules, atoms, and/or ions forming the crystal.

The term "pharmaceutically acceptable salt" refers to any pharmaceutically acceptable salt which, upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

More specifically, in the present invention compounds are derivatives of cannabigerol-hydroxy-quinone derivatives (CBG-Q derivatives) of Formula (I):

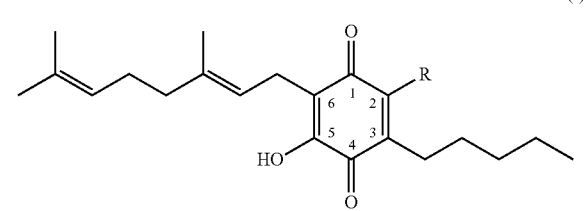

(I)

wherein R is the carbon atom of a group, represented by: aryl, linear or branched alkenyl, linear or branched alkynyl, or linear or branched alcoxycarbonyl groups; or wherein R is the nitrogen atom of a group, represented by: linear or branched alkylamino, arylamino, linear or branched alkenylamino, or linear or branched alkynylamino groups; or, alternatively, R represents a bond between 2 molecules of formula (I) forming a dimer. In a preferred embodiment, the compounds of the invention are those of Formula (II), (III), (IV), (V), (VI), (VII), (VIII), (X), (XI) and (XII).

(II)

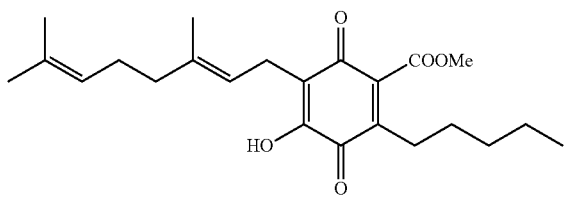

6-(3,7-dimethyl-octa-2, 6-dienyl)-5-hydroxy-3-pentyl-2-metoxycarbonil-[1,4]benzoquinone (III)

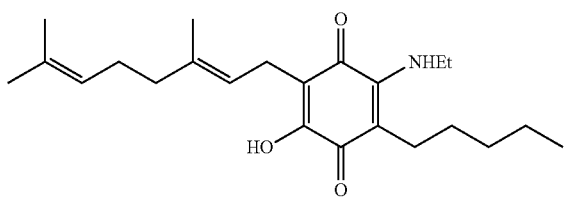

6-(3,7-dimethyl-octa-2,6-dienyl)-5-hydroxy-3-pentyl-2-ethylamino-[1,4]benzoquinone (IV)

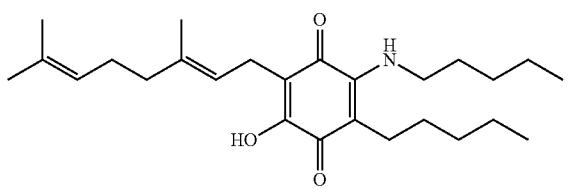

6-(3,7-dimethyl-octa-2,6-dienyl)-5-hydroxy-3-pentyl-2-pentylamino-[1,4]benzoquinone (V)

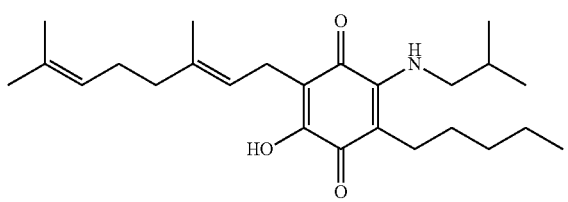

6-(3,7-dimethyl-octa-2, 6-dienyl)-5-hydroxy-3-pentyl-2-isobutylamino [1,4]benzoquinone (VI)

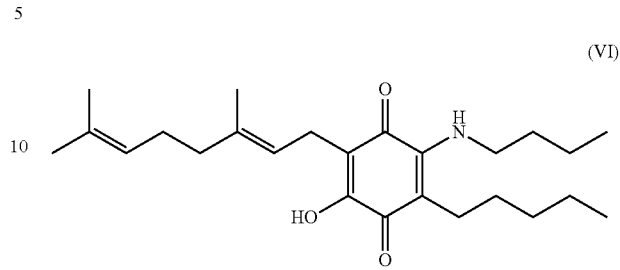

6-(3,7-dimethyl-octa-2,6-dienyl)-5-hydroxy-3-pentyl-2-butylamino [1,4]benzoquinone (VII)

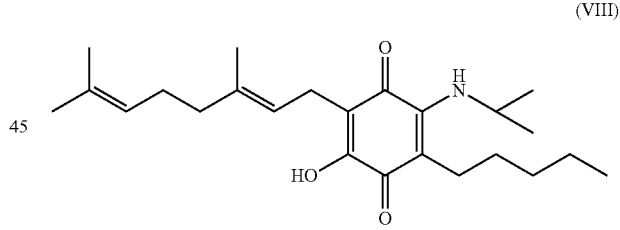

6-(3,7-dimethyl-octa-2,6-dienyl)-5-hydroxy-3-pentyl-2-methylamino-[1,4]benzoquinone (VIII)

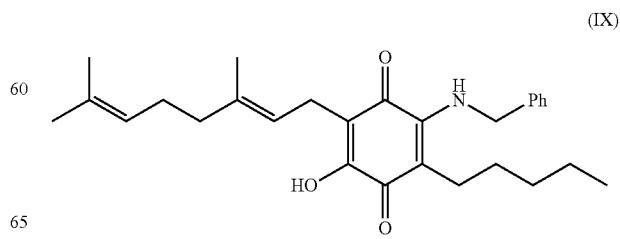

6-(3,7-imethyl-octa-2,6-dienyl)-5-hydroxy-3-pentyl-2-isopropylamino-[1,4]benzoquinone (IX)

6-(3,7-dimethyl-octa-2,6-dienyl)-5-hydroxy-3-pentyl-2-benzylamino [1,4]benzoquinone (X)

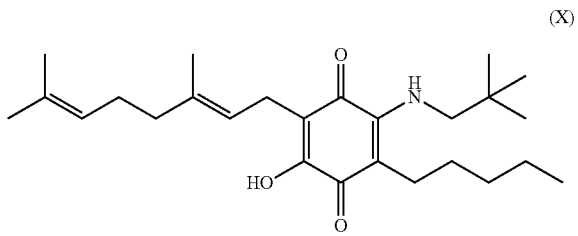 [SMILES: CCCCCC1=C(NCC(C)(C)C)C(=O)C(C/C=C(\C)CCC=C(C)C)=C(O)C1=O]

6-(3,7-dimethyl-octa-2,6-dienyl)-5-hydroxy-3-pentyl-2-(2,2-dimethyl-propylamino)-[1,4]benzoquinone (XI)

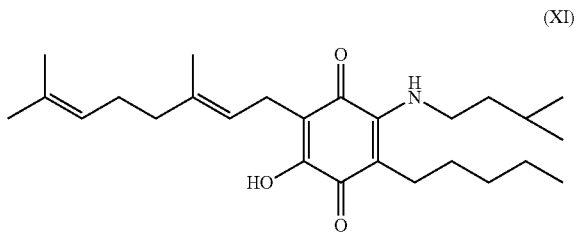 [SMILES: CCCCCC1=C(NCCC(C)C)C(=O)C(C/C=C(\C)CCC=C(C)C)=C(O)C1=O]

6-(3,7-dimethyl-octa-2,6-dienyl)-5-hydroxy-3-pentyl-2-(3-methyl-butylamino)-[1,4]benzoquinone (XII)

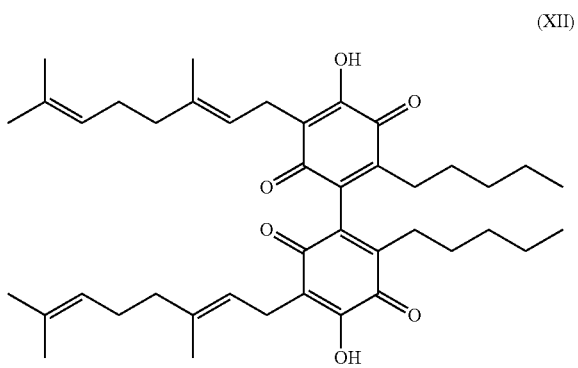 [SMILES: CCCCCC1=C(C2=C(CCCCC)C(=O)C(O)=C(C/C=C(\C)CCC=C(C)C)C2=O)C(=O)C(C/C=C(\C)CCC=C(C)C)=C(O)C1=O]

3,3'-bis((E)-3,7-dimethyl-octa-2,6-dienyl)-4,4'-dihydroxy-6,6'-dipentyl-1,1'-bi(cyclohexa-3,6-diene)-2,2',5,5'-tetraone As it will be inferred below from the examples and figures, the modifications in position 2 comprised in the general Formula I confer the compounds of the present invention the capacity to activate to PPARg and to protect from glutamate-induced cytotoxicity. These compounds also shown a remarkable low cytotoxicity in cell lines of neuronal origin compared with CBG-Q (compound I) comprised in the state of the art. In addition compounds III and XII), as representative from this series, showed therapeutic efficacy in animal models of diseases (Multiple Sclerosis, Parkinson and Huntington diseases) widely used to evaluate the clinical efficacy of PPARg agonists.

CBG-Q, the compound I, is the precursor of all the derivatives of Formula I of present invention, exemplified by compounds II to XII. CBG-Q precursor can be initially synthetized by starting from natural cannabinoids such as CBG (cannabigerol) and CBGA (cannabigerol acid) by means of the substitution of some specific radicals.

References to cannabigerol hydroxy quinone derivatives will be understood to also encompass pharmaceutically acceptable salts of such compounds. The term "pharmaceutically acceptable salts" refers to salts or esters prepared from pharmaceutically acceptable bases or acids, including inorganic bases or acids and organic bases or acids, as would be well known to any person skilled in the art.

A further embodiment of the present invention refers to the use of compounds of Formula (I) or derivatives thereof as medicaments, particularly as PPARg agonists of the PPARg receptors which do not induce Nfr2 activation, particularly in the treatment of diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists.

Other embodiment of the present invention refers to the use of compounds of Formula (I) for the manufacture of a composition for treating PPRAg related diseases with lower citotoxicity such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists.

An alternative embodiment of the present invention refers to the use of the above mentioned compounds of Formula (I) or derivatives, alone or formulated in compositions, particularly pharmaceutical compositions, that comprise at least one of the compounds of the invention combined with at least another active compound having additive or synergistic biological activities. Alternatively said compositions can be formulated with at least one inert ingredient as a carrier or excipient such as: cosolvents, surfactants, oils, humectants, emollients, preservatives, stabilizers and antioxidants. Any pharmacologically acceptable buffer may be used, e. g., TRIS or phosphate buffers.

For the purposes of present description the term "active compound or active principle" should be taken as synonyms and mean a chemical entity which exerts therapeutic effects when administered to human or animal beings.

Typical compositions include the compounds of the invention, or derivatives thereof, associated with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compound of interest will usually be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The composition could be used for the treatment of diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists One preferred embodiment of the present invention refers to the route of administration, that may be any route which effectively transports the compound of interest to the appropriate or desired site of action, such as oral, nasal, topical, pulmonary, transdermal or parenteral, e. g., rectal, subcutaneous, intravenous, intraurethral, intramuscular, intranasal, ophthalmic solution or an ointment.

For nasal administration, the preparation may contain the compound of interest dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical formulations, the compound interest is placed in a dermatological vehicle as is known in the art. The amount of the compound of interest to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of interest and selects the amount of formulation administered, depending upon clinical experience with the patient in question or with similar patients.

For ophthalmic applications, the compound of interest is formulated into solutions, suspensions, and ointments appropriate for use in the eye. The concentrations are usually as discussed above for local preparations.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of interest with an inert pharmaceutical diluent and filling the mixture into a hard gelatin capsule of appropriate size. Soft gelatin capsules are prepared by machine encapsulation of slurry of the compound of interest with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravascular, and subcutaneous.

In addition to the compound of interest, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts that are effective to obtain a pharmaceutically acceptable formulation in terms of solubility, biological activity, etc.

The compound of interest may be incorporated into a microsphere. The compound of interest can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e. g., with petroleum ether followed by ethanol. Finally, the microspheres can be sieved and collected and dried by filtration.

Starch microspheres can be prepared by adding a warm aqueous starch solution, e. g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The microspheres can be hardened by well known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Another preferred embodiment of the invention is the dosage scheme. The term "unit dosage form" refers to physically discrete units suitable as unitary dosages for subjects, e. g, mammalian subjects, e. g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

An effective amount of the compound of interest is employed in treatment. The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

A last embodiment of the present invention refers to a method for treating diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity and Type II diabetes, which can be treated with PPARg agonists; that comprises the administration to the patient of an effective amount of the above composition.

ABBREVIATIONS

CBG: Cannabigerol.
CBGA: Cannabigerol acid.
CBG-Q (compound I): Cannabigerol hydroxy quinone.
DCC: dicyclohexylcarbodiimide.
Keap1: Kelch ECH associating protein 1.
NFE2L2 or (Nrf2): Nuclear factor (erythroid-derived 2)-like 2.
NR1C: Nuclear subfamily 1 C.
NRs: Nuclear receptors.
PPARs: Perixome proliferator activated receptors.
PPARg: Peroxisome proliferator-activated receptor gamma also called PPARγ, glitazone receptor or NR1C3.
PPARα: Peroxisome proliferator-activated receptor alfa also called NR1C1.
PPARβ/δ: Peroxisome proliferator-activated receptor beta/delta also called NR1C2.

DESCRIPTION OF FIGURES

The figures of the invention are briefly described below. An in deep explanation of each figure is included in every pertinent example.

FIGURES ABBREVIATIONS

I: refers to CBG-Q.
II: refers to compound of formula (II).
III: refers to compound of formula (III).
IV: refers to compound of formula (IV).
V: refers to compound of formula (V).
VI: refers to compound of formula (VI).
VII: refers to compound of formula (VII).
VIII: refers to compound of formula (VIII).
IX: refers to compound of formula (IX).
X: refers to compound of formula (X.
XI: refers to compound of formula (XI).
XII: refers to compound of formula (XII).

Figure 1A:
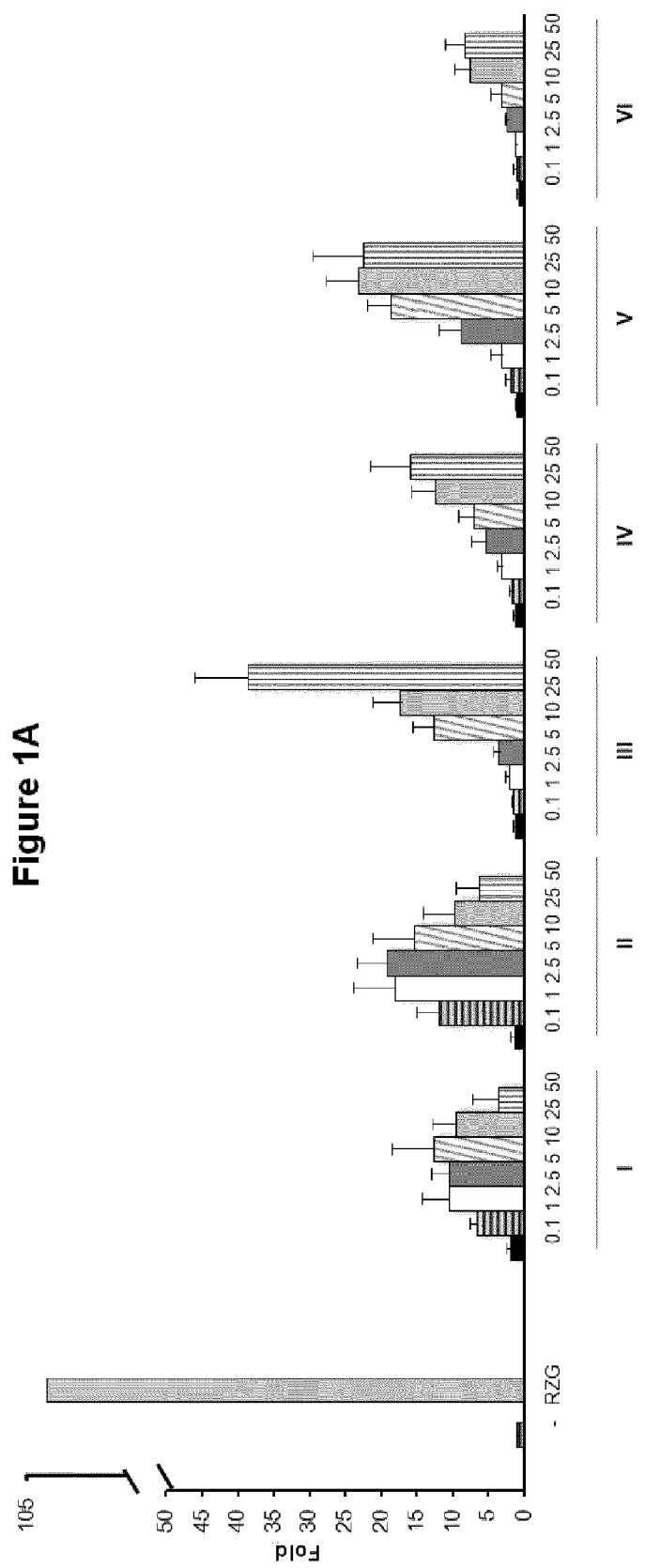
Figure 1B:
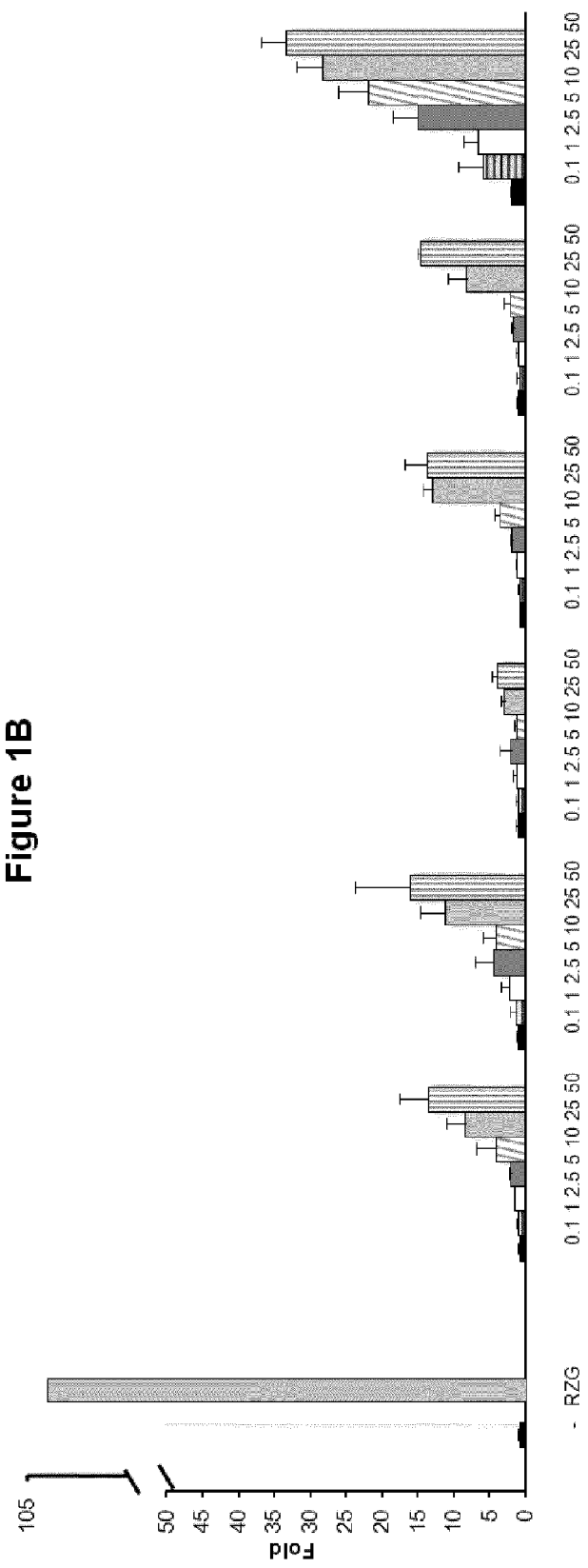

FIG. 1. PPARg Transactivation Assays in HEK-293 Cells

The concentration of the tested compound (μM) is shown at the x-axis and the PPARg activation fold is shown at the y-axis. This figure shows the effect of CBG-Q or compound I versus the effect of compounds II-VI (FIG. 1A) and versus the effect of compounds VII-XII (FIG. 1B) on PPARg activity, ratifying that derivatives of CBG-Q (compound I), and specially compounds II, III, IV, V, VII, VIII, and XII, are being able to induce PPARg activation with higher efficiency than CBG-Q (compound I). The PPARγ full agonist Rosiglitazone (RZG) 1 μM was used as comparative control. Fold activation level was calculated, taking the control sample (−), without the presence of any PPARg agonist or activating agent, as reference. Data are expressed as mean±S.D. of at least three independent experiments.

Figure 2:
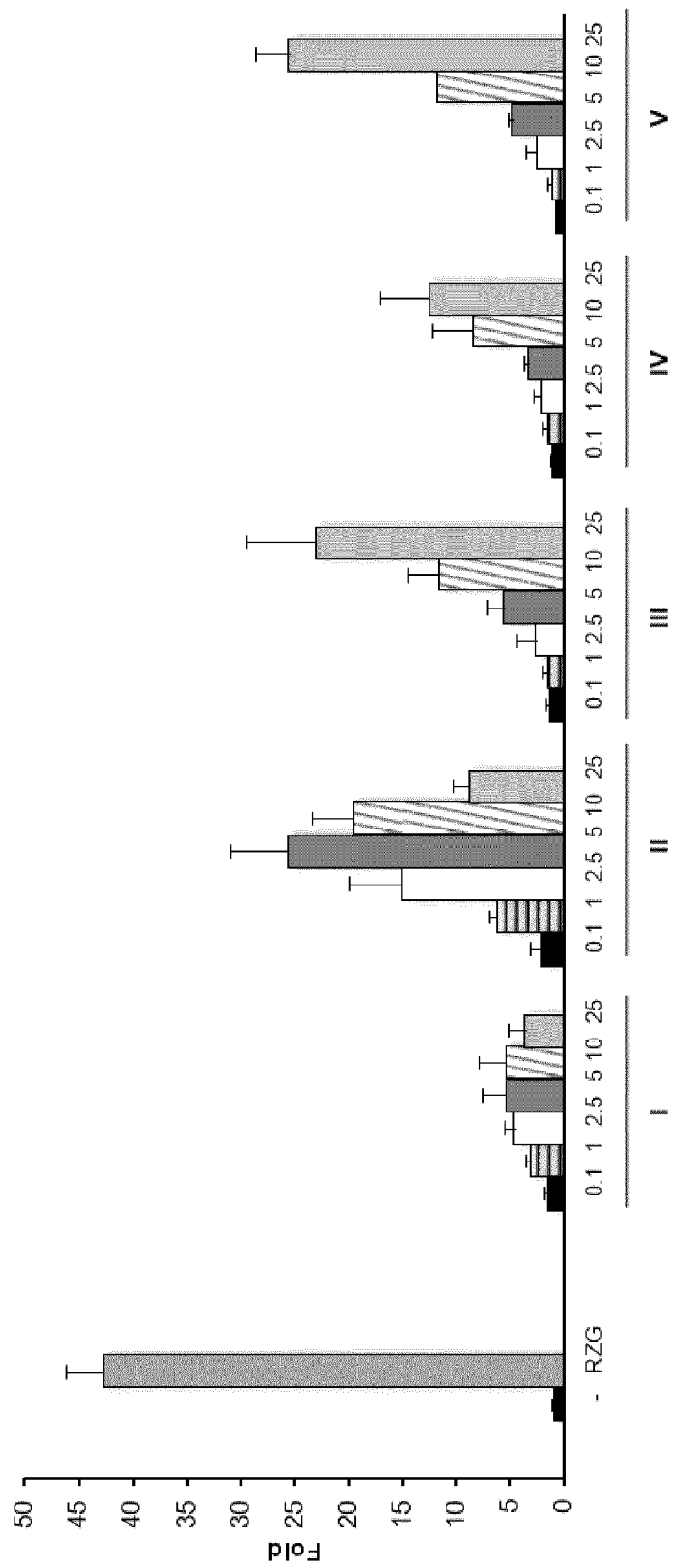

FIG. 2. PPARg Transactivation Assays in Human Dermal Primary Fibroblasts.

The concentration of the tested compound (μM) is shown at the x-axis and the PPARg activation fold is shown at the y-axis. This figure shows the effect of CBG-Q (compound I) versus compounds II, III, IV, and V on PPARg activity, ratifying that those compounds II, III, IV, and V are being able to induce PPARg activation with higher efficiency than CBG-Q (compound I). The PPARγ full agonist Rosiglitazone (RZG) 1 μM was used as comparative control. Fold activation level was calculated, taking the control sample (−), without the presence of any PPARg agonist or activating agent, as reference. Data are expressed as mean±S.D. of at least three independent experiments.

Figure 3:
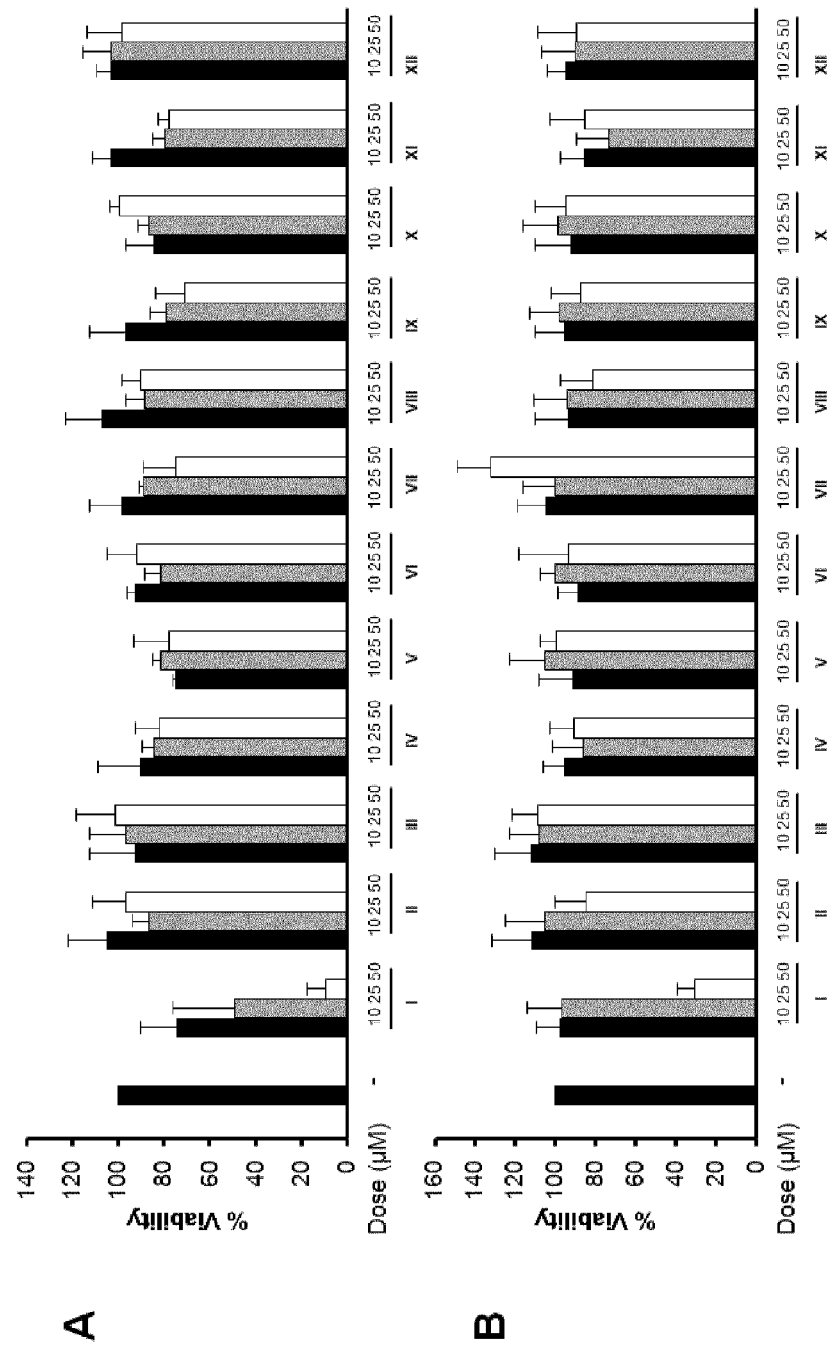
Figure 3:
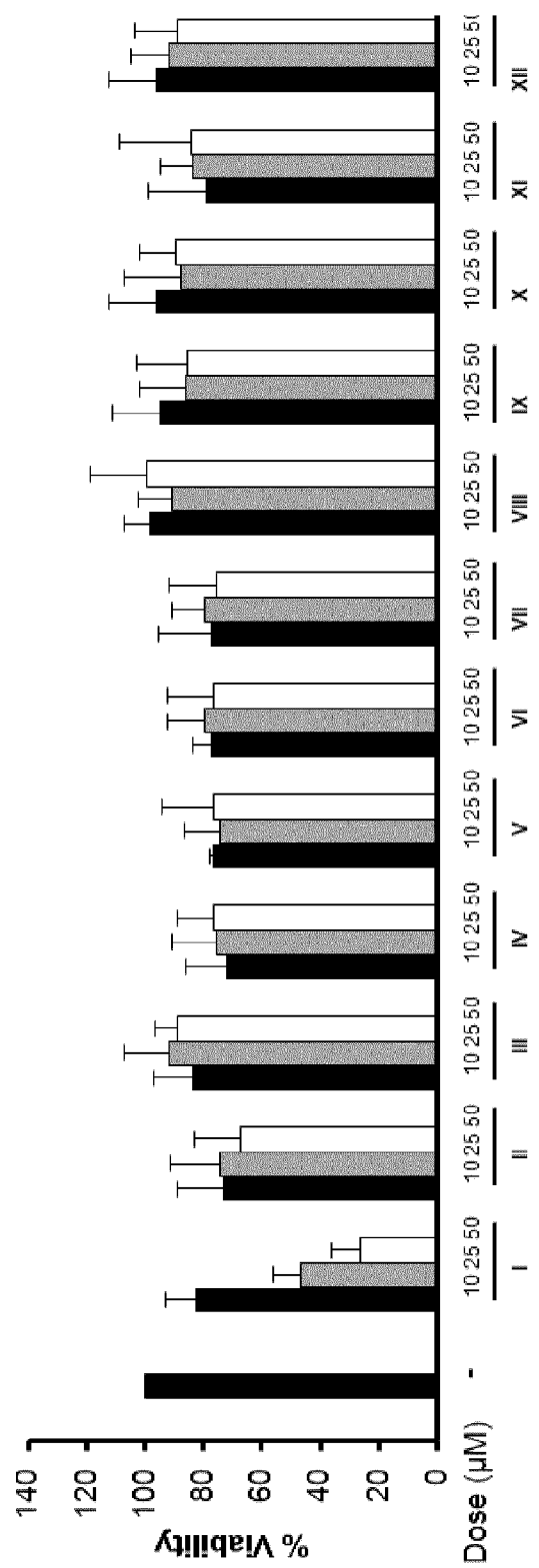

FIG. 3. Cytotoxicity Activity.

The cell lines N2a (A), HT22 (B) and MO3.13 (C) cells were incubated for 24 h with the indicated doses of CBG-Q (Compound I) versus compounds II to XII, and cell viability was quantified by MTT assay. Results are shown as mean±S.D. from at least three independent experiments, and expressed as percentage of cell viability against the control sample (−), without the presence of any PPARg agonist or activating agent. Control was set as 100% and data were referred to that value. The results demonstrate that the cytotoxic activity associated to CBG-Q (compound I) is missing in all the CBG-Q derivatives in position 2 described in the present invention.

FIG. 4. Nrf2 Transcriptional Assays

HaCaT-ARE-Luc cells were incubated for 6 h with compounds CBG-Q compound I) and with compounds I to VI (A) or with compounds VII to XII (B) at the indicated concentrations, and protein lysates were prepared and analysed for luciferase activity. The pro-oxidant tert-Butylhydroquinone (tBHQ) at 20 μM, a compound that induces cellular oxidative stress, was used as positive control. Fold activation level was calculated, taking the control sample (−), without the presence of any PPARg agonist or activating agent, as reference. Data are expressed as mean±S.D. from at least three independent experiments. The results ratify that the reactive electrophilic activity associated to CBG-Q (compound I) is missing in all the compounds (derivatives in position 2) described in the present invention.

Figure 5:
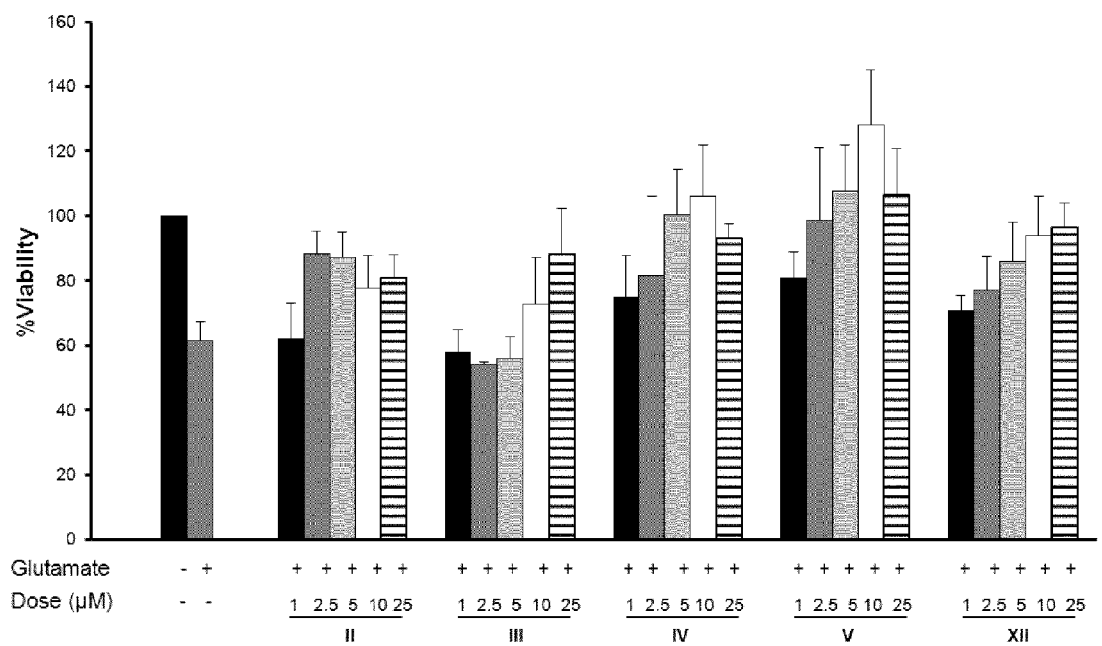

FIG. 5. Neuroprotective Activity.

N2a cells were pre-incubated for 1 h with compounds (II) to (V) and (XII) at the indicated concentrations. Then, cells were treated for 24 h with 5 mM glutamate to induce excitotoxicity, or cytotoxicity in neuronal cells induced by neurotransmitters. Cell viability was quantified by MTT assay. Results are shown as mean±S.D. from at least three independent experiments, and expressed as percentage of cell viability against the control sample (−), without the presence of any PPARg agonist or activating agent and with (−,+) or without (−,−) glutamate. Control was set as 100% and data were referred to that value.

Figure 6:
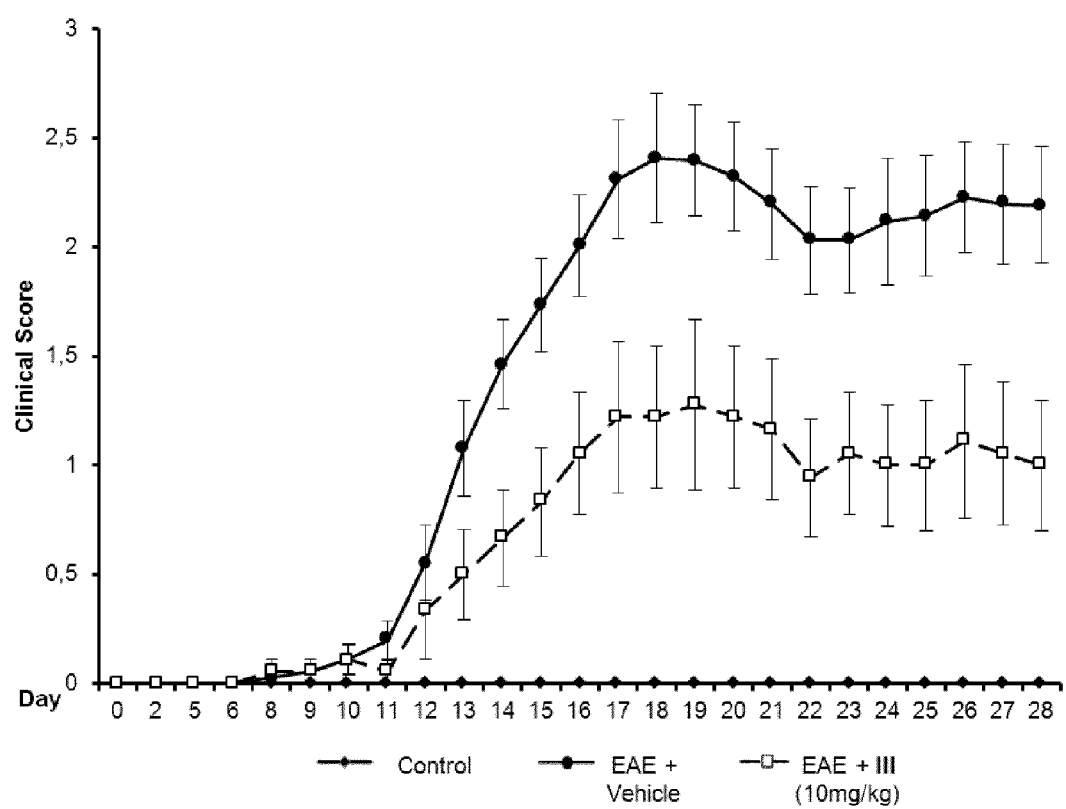

FIG. 6. Compound (III) Alleviates EAE

C57BL/6 mice were immunized with MOG$_{35-55}$ and their clinical score evaluated daily. Mice were treated daily with compound (III) (10 mg/kg) on day 6 post-immunization and the 21 following days. The graph shows the daily average clinical score (mean±SEM). Values are expressed as means±SEM for 10 animals per group.

Figure 7:
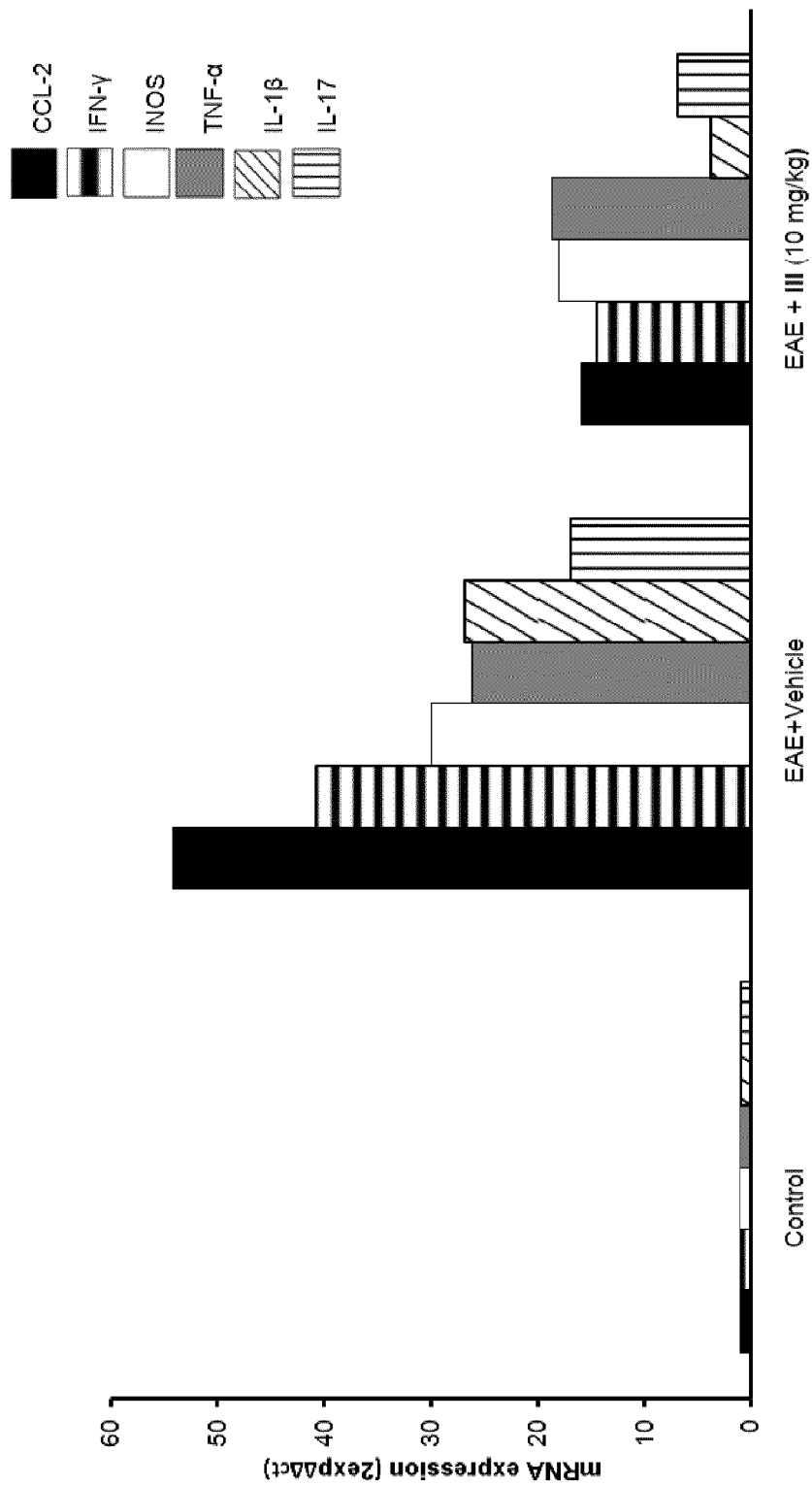

FIG. 7. Effect of compound (III) on pro-inflammatory markers (EAE)

Gene expression of inflammatory markers including CCL2, IFNγ, INOS, TNFα, IL-1β and IL-17 in the spinal cord was down regulated in EAE+compound (III) (10 mg/kg) group compared with EAE+Vehicle mice. Expression levels were calculated using the $2^{-\Delta\Delta ct}$ method.

Figure 8:
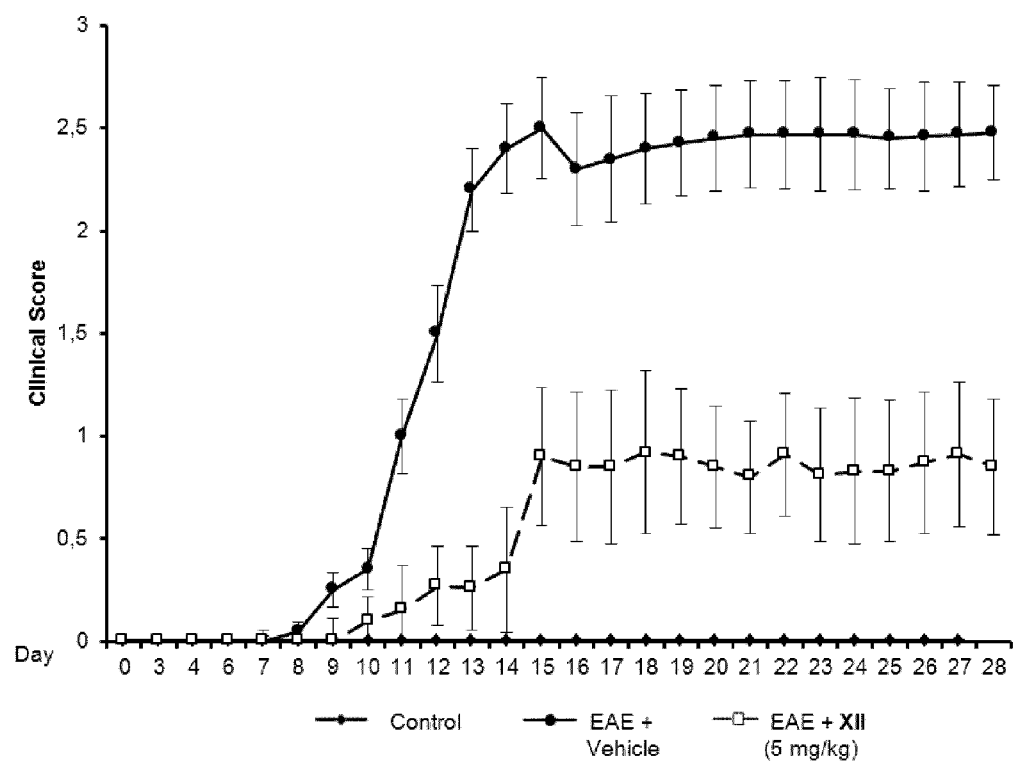

FIG. 8. Compound (XII) Alleviates EAE

C57BL/6 mice were immunized with MOG$_{35-55}$ and their clinical score evaluated daily. Mice were treated daily with compound (XII) (5 mg/kg) on day 6 post-immunization and the 21 following days. The graph shows the daily average clinical score (mean±SEM). Values are expressed as means±SEM for 6 animals per group.

Figure 9:
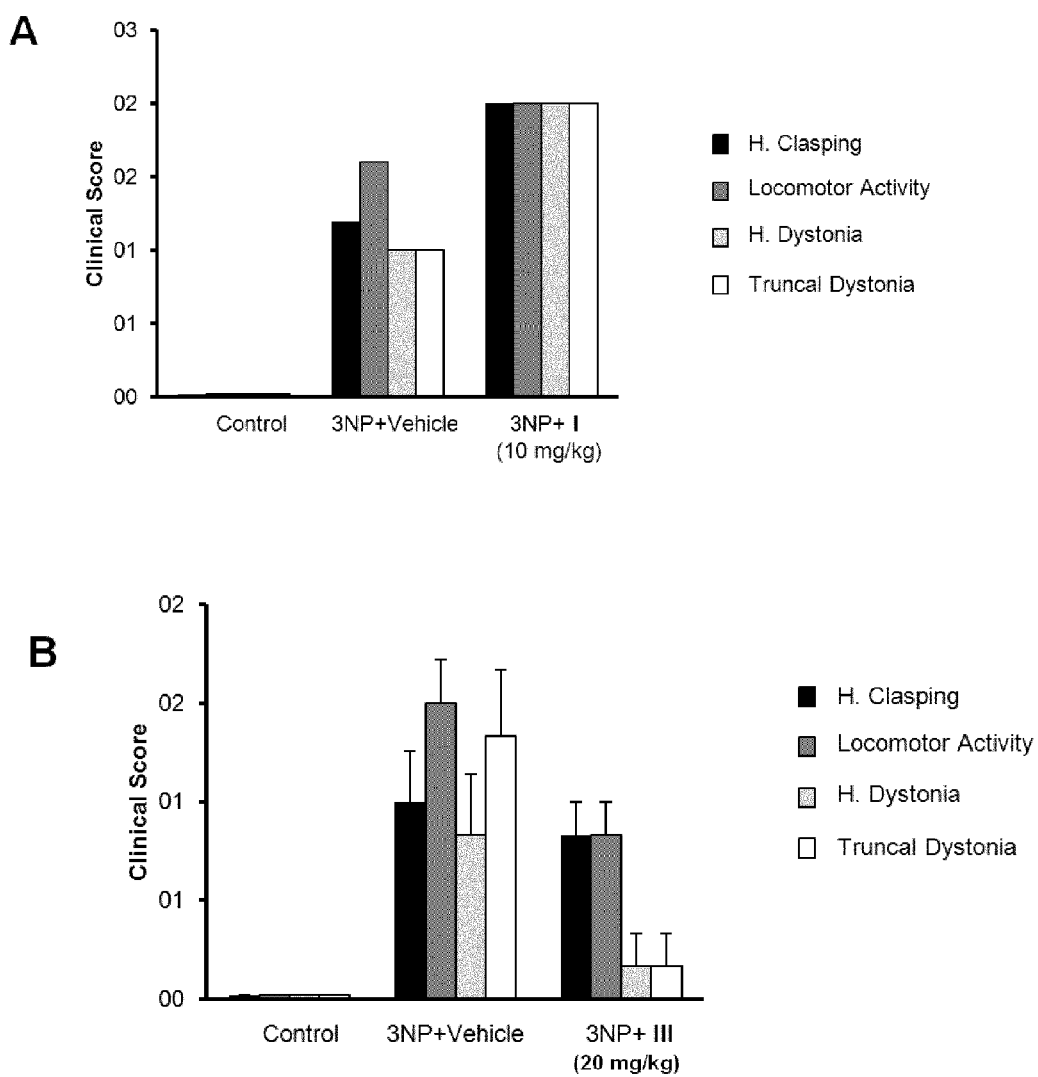
Figure 9:
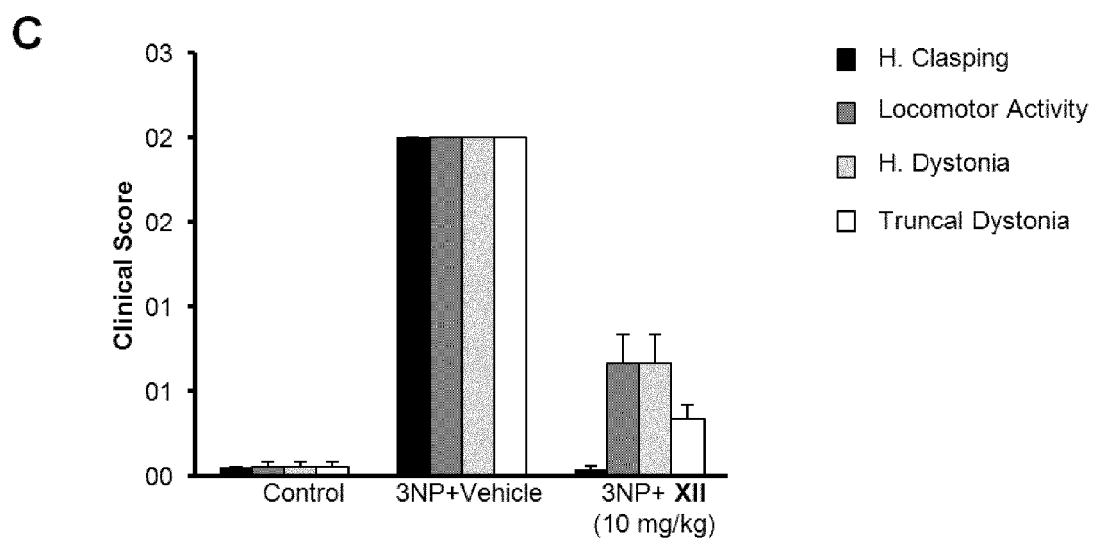

FIG. 9. Behavioral Score after 3NP Intoxication.

Mice were subjected to behavioral tests for determining their neurological status after the treatment with compounds I (10 mg/kg) (A), III (10 mg/kg) (B) and XII (10 mg/kg) (C). Hind limb clasping, Locomotor activity, Hind limb dystonia and Truncal Dystonia were rated from 0 to 2 based on severity: a score of 0 typically indicates normal function and 2 seriously affected. Values are expressed as means±SEM for 8 animals per group.

FIG. 10. Compound III Reduces the Expression on Inflammatory Marker mRNAs in the Striatum.

Gene expression of inflammatory markers including COX-2, TNFα, IL-6 and iNOS, was down regulated in 3NP+compound III (10 mg/kg) treated mice compared with 3NP+Vehicle mice. Expression levels were calculated using the $2^{-\Delta\Delta ct}$ method. Values are expressed as means±SEM for 6 animals per group.

Figure 11:
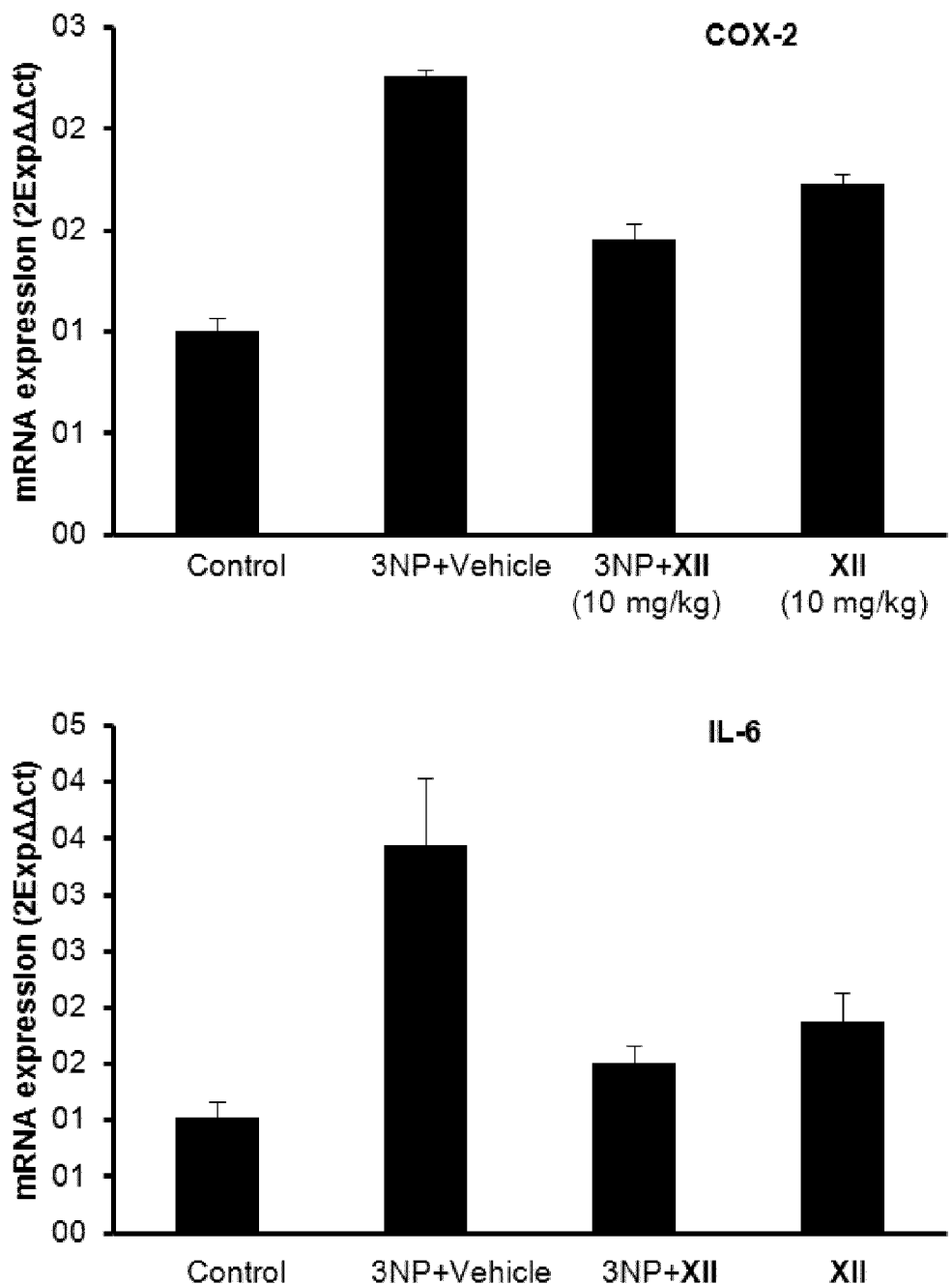

FIG. 11. Compound XII Reduces the Expression on Inflammatory Marker mRNAs in the Striatum.

Gene expression of inflammatory markers including COX-2, TNFα, IL-6 and iNOS, was down regulated in 3NP+XII (10 mg/kg) treated mice compared with 3NP+Vehicle mice. Expression levels were calculated using the $2^{-\Delta\Delta ct}$ method. Values are expressed as means±SEM for 6 animals per group.

Figure 12:
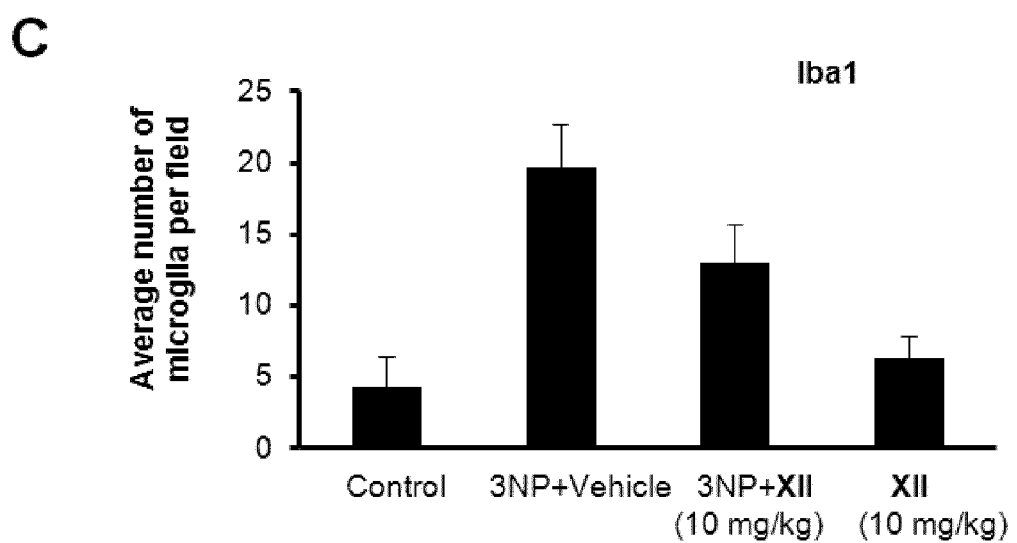

FIG. 12. Effect of Compound XII on Neurodegenerative Markers (3NP)

NeuN (neuronal marker), GFAP (astrocytes marker), and Iba1 (microglia marker) were detected by immunostaining in the coronal sections of striatum of mice treated with vehicle, 3NP+ vehicle, 3NP+compoundXII (10 mg/kg) and XII (10 mg/kg). Quantification of NeuN (A), GFAP (B) and Iba1 (C) positive cells in the mouse striatum. Total average number of neurons, astrocytes and microglia is shown. Values are expressed as means±SEM for 6 animals per group.

Figure 13:
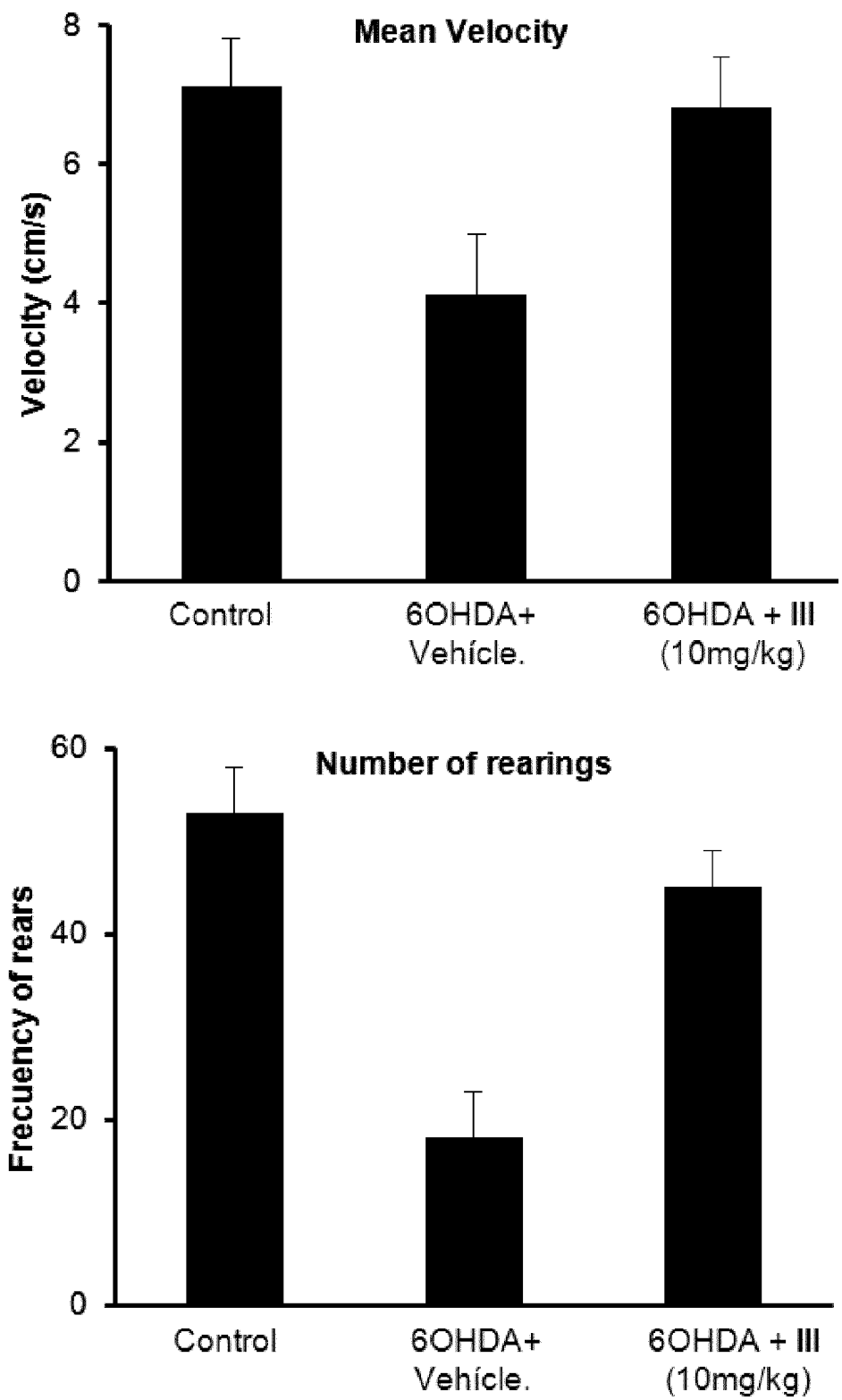
Figure 13:
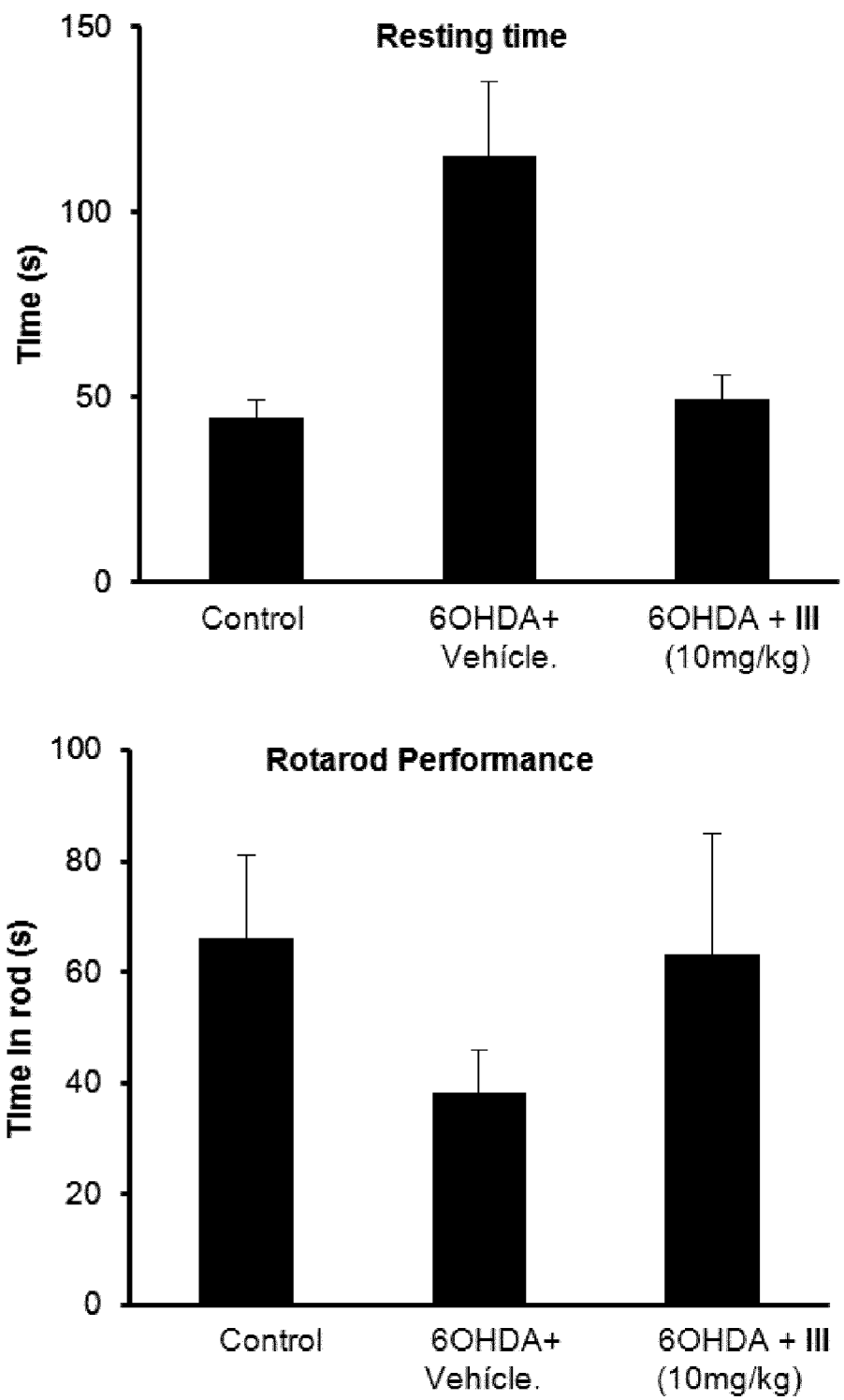

FIG. 13. Effect of Compound (III) on 6-OHDA-Induced Parkinson Symptomatology.

C57BL/6 mice were unilaterally injected intracerebroventricullarly with 6-hydroxydopamine (6-OHDA) or saline (control mice) and subjected to chronic intraperitoneal treatment with compound III (10 mg/ml) or vehicle (14 days), starting 16 h after the 6-OHDA injection. Motor coordination was evaluated by rotarod performance and motor activity was evaluated using a computer-aided actimeter. Values are expressed as means±SEM for 6 animals per group.

EXAMPLES

The examples of the present invention described below aim to illustrate its preferred embodiments without limiting its scope of protection.

Example 1. Chemical Synthesis and NMR Analysis

General Procedures for Compounds Derived from CBGA. Synthesis of Compounds (II) and (XII))

To a solution of CBGA (Cannabigerol acid) (360 mg, 0.80 mmol) in methanol (10 mL), dicyclohexylcarbodiimide (DCC) (331 mg, 1.6 mmol) and catalytic p-toluenesulfonic acid (ca. 10 mg) were added. After stirring for 40 min, the reaction was worked up by evaporation (Scheme 1). The residue was dissolved in toluene (ca 10 mL), and cooled (−18° C.) to precipitate the urea. After 1 h, the solution was filtered on a sintered glass filter, and the residue purified by flash chromatography of RP C-18 silica gel to afford 260 mg of (E)-methyl 3-(3,7-dimethylocta-2,6-dienyl)-2,4-dihydroxy-6-pentylbenzoate [colorless foam, yield: 70%].

$^1$H NMR (CDCl$_3$, 300 MHz) δ ppm 12.00 (bs, 1H), 6.25 (s, 1H), 5.27 (bt, J=6.5 Hz, 1H), 5.04 (bt, J=6.5 Hz, 1H), 3.90 (s, 3H), 3.41 (d, J=6.8 Hz, 1H), 2.05 (bm, 4H), 1.80 (bs, 3H), 1.66 (bs, 3H), 0.89 (t, J=6.0 Hz, 3H).

Scheme 1

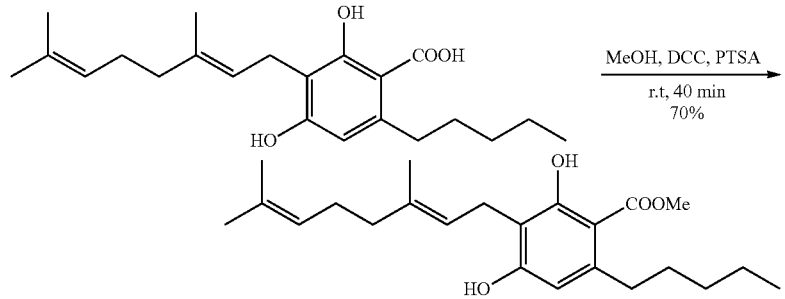

Preparation Compound II 6-(3,7-dimethyl-octa-2, 6-dienyl)-5-hydroxy-3-pentyl-2-metoxycarbonil-[1,4]benzoquinone Scheme 2

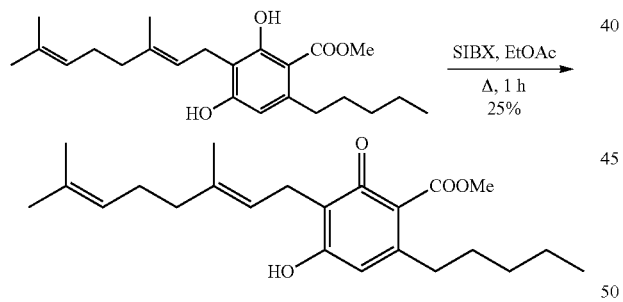

To a solution of 100 mg (0.27 mmol) of (E)-methyl 3-(3,7-dimethylocta-2,6-dienyl)-2,4-dihydroxy-6-pentylbenzoate in 4 mL EtOAc, SIBX (465 mg, 0.77 mmol, 3 mol equiv.) was added, and the reaction was refluxed for 1 h. After cooling and filtration over Celite, the filtrate was sequentially washed with sat. NaHCO$_3$ and brine. After drying (Na$_2$SO$_4$) and evaporation, the residue was purified by column chromatography on silica gel (petroleum ether-CH2Cl2 8:5 as eluent) to afford mg 6-(3,7-dimethyl-octa-2,6-dienyl)-5-hydroxy-3-pentyl-2-metoxycarbonill-[1,4] benzoquinone. [brown-colored solid, yield: 25%].

$^1$H NMR (CDCl3, 300 MHz) δ ppm 6.95 (bs, 1H), 5.11 (bt, J=6.5 Hz, 1H), 5.04 (bt, J=6.5 Hz, 1H), 3.89 (s, 3H), 3.13 (d, J=6.5 Hz, 2H), 2.38 (m, 2H), 1.72 (bs, 3H), 1.65 (bs, 3H), 1.57 (bs, 3H), 0.89 (t. J=6.5 Hz, 3H).

Preparation Compound XII 3,3'-bis((E)-3,7-dimethylocta-2,6-dienyl)-4,4'-dihydroxy-6,6'-dipentyl-1,1'-bi(cyclohexa-3,6-diene)-2,2',5,5'-tetraone Scheme 3

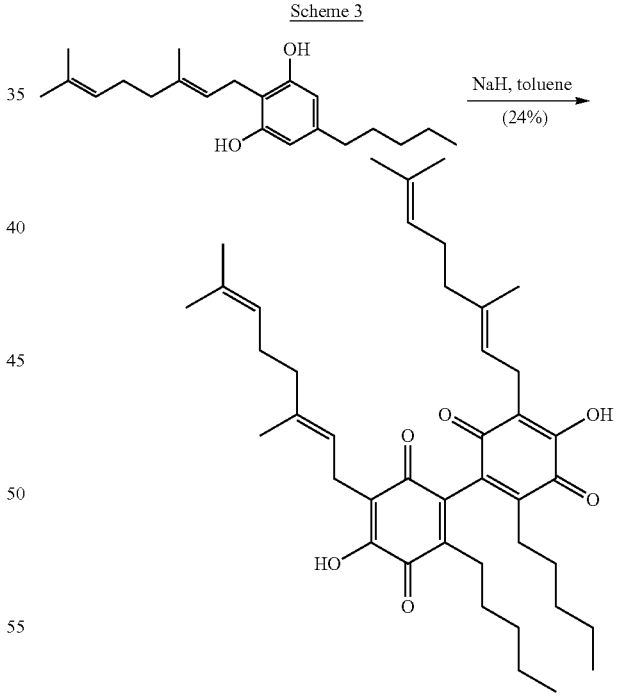

To a solution of cannabigerol (CBG) (500 mg, 0.16 mmol) in toluene (100 mL), NaH (95%, 150 mg, 0.48 mmol, 3 mol. equiv) was added, and the reaction was stirred vigorously leaving the flask open (Scheme 3). A violet color developed almost instantaneously, and after 12 h the reaction was worked up by acidification with 2N H$_2$SO$_4$ to pH 3, and partition between brine and EtOAc. The organic phase was dried (Na$_2$SO$_4$) and evaporated, and the residue was purified by gravity column chromatography on silica gel (petroleum ether-EtOAc 9:1 as eluant) to afford 120 mg 3,3'-bis((E)-3,7-dimethylocta-2,6-dienyl)-4,4'-dihydroxy-6,6'-dipentyl-1,1'-bi (cyclohexa-3,6-diene)-2,2',5,5'-tetraone [brown dark gum, yield: 24%].

$^1$H NMR (CDCl$_3$, 300 MHz) δ ppm: 6.99 (bs, 2H), 5.10 (bt, J=6.5 Hz, 2H), 5.05 (bt, J=6.5 Hz, 2H) 3.13 (d, J=6.5 Hz, 4H), 1.71 (s, 6H), 1.65 (s, 6H), 1.57 (s, 6H), 0.81 (t, J=7.0 Hz, Example 2. Chemical Synthesis and NMR Analysis General Procedures for Compounds Derived from CBG. Synthesis of Compounds (III) to (XI))

Synthesis of CBG-Q (compound I) starting from CBG (Cannabigerol) was carried out by using tBuOK in toluene, at r.t., in the presence of air (Scheme 4)

Scheme 4

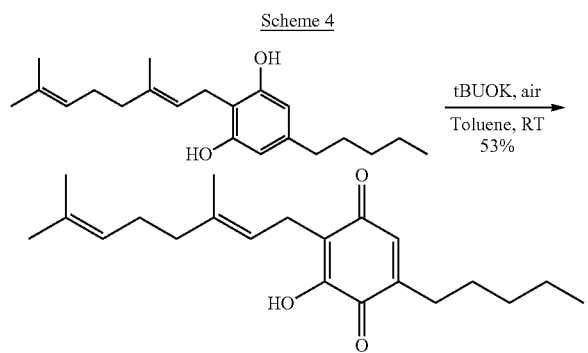

tBuOK (2.00 g, 17.824 mmol) was added to a solution of Cannabigerol (CBG) (2.00 g, 6.319 mmol) in toluene (400 mL), to give a purple-colored solution. The reaction mixture was stirred at r.t., in an air-opened round bottom flask, and conversion was monitored by TLC analysis (eluent: 10% EtOAc/hexanes) (Scheme 5). After 2 h, the reaction mixture was washed with HCl (5% aqueous solution, 300 mL) and the aqueous layer was extracted with EtOAc (100 mL). Combined organic layers were dried over Na$_2$SO$_4$ (anhydrous), filtered and concentrated. The crude residue was flash chromatographed on SiO$_2$ (2 to 4% EtOAc/hexanes), to give 1.10 g of CBG-Q (compound I) [orange-colored solid, yield: 53%].

$^1$H NMR (CDCl$_3$, 300 MHz): δ 6.94 (s, —OH, 1H), 6.45 (s, 1H), 5.13 (br t, J=6.8 Hz, 1H), 5.04 (br t, J=6.8 Hz, 1H), 3.14 (s, J=6.8 Hz, 2H), 2.41 (t, J=7.8 Hz, 2H), 2.09-1.92 (m, 4H), 1.73 (br s, 3H), 1.57 (br s, 3H), ca. 1.52 (m, 2H), 1.38-1.17 (m, 4H), 0.89 (t, J=7.8 Hz, 3H).

Synthesis of derivatives substituted at position 2 with alkylamino, arylamino, alkenylamino or alkynylamino was accomplished by reacting CBG-Q (compound I) with a large excess of amine, at r.t., in an air-opened reaction system (Scheme 5)

Scheme 5

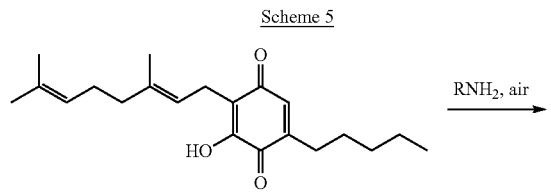

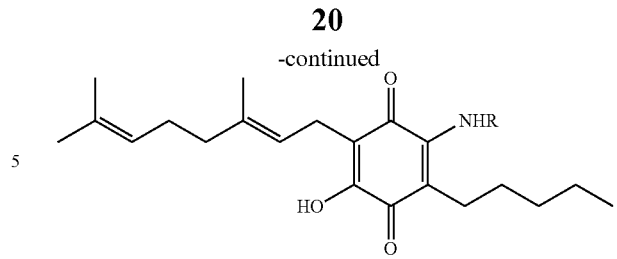

High conversion was achieved within several hours, to give spot to spot reactions. Solvent was concentrated off, and the crude residue was purified by reverse phase chromatography, to give products with purities about 95%.

Preparation of Compound III 6-(3,7-dimethyl-octa-2,6-dienyl)-5-hydroxy-3-pentyl-2-ethylamino-[1,4]benzoquinone Scheme 6

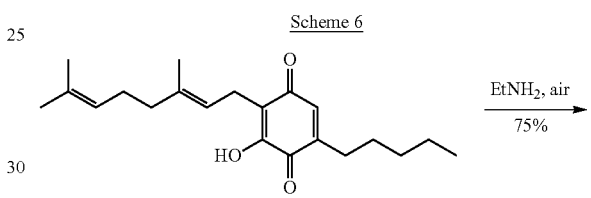

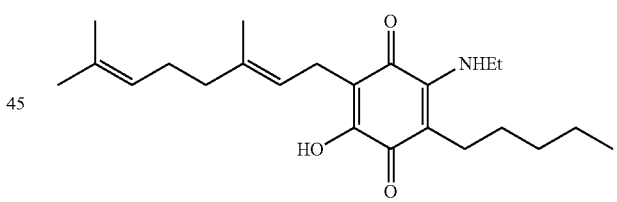

Ethylamine (5.2 mL, 70% solution in H$_2$O, 65.403 mmol) was added to a solution of CBG-Q (compound I) (510 mg, 1.543 mmol) in EtOH (50 mL). The reaction mixture was stirred at r.t. for 2 h (Scheme 6). It was poured into H$_2$O (120 mL), taken up to pH=2 with HCl (10% aqueous solution) and extracted with CH$_2$Cl$_2$ (2×80 mL). The organic layer was dried over Na$_2$SO$_4$ (anhydrous), filtered and concentrated. Crude residue was purified by reverse phase chromatography (30 to 100% CH$_3$CN/H$_2$O) to give 435 mg of 2-(3,7-dimethyl-octa-2,6-dienyl)-6-ethylamino-3-hydroxy-5-pentyl-[1,4]benzo-quinone [purple-colored solid, yield: 75%].

$^1$H NMR (CDCl$_3$, 300 MHz) δ ppm: 6.39 (bs, 1H), 5.09 (m, 2H), 3.54 (t, J=6.6 Hz, 2H), 3.05 (d, J=6.6 Hz, 2H), 2.49 (m, 2H), 1.99 (m, 4H), 1.72 (s, 3H), 1.64 (s, 3H), 1.57 (s, 3H), 1.44-1.22 (m, 9H), 0.88 (m, 3H).

Preparation Compound IV

6-(3,7-dimethyl-octa-2,6-dienyl)-5-hydroxy-3-pentyl-2-pentylamino-[1,4]benzoquinone Scheme 7

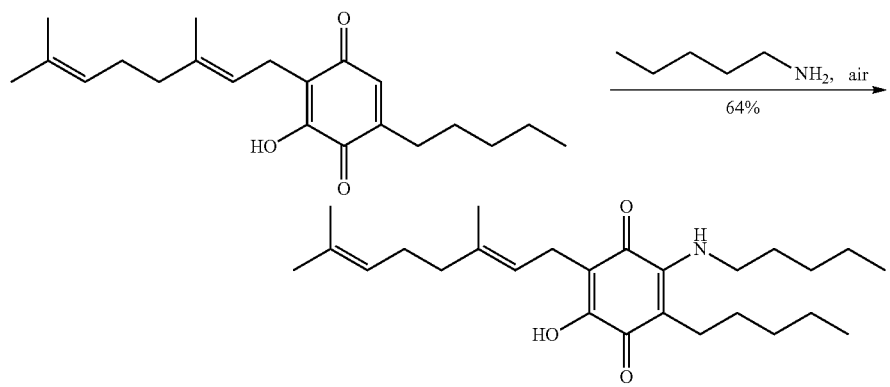

Amylamine (1.5 mL, 12.943 mmol) was added to a solution of compound CBG-Q (compound I) (109 mg, 0.330 mmol) in EtOH (10 mL). The reaction mixture was stirred at r.t. for 22 h (Scheme 7). It was poured into H$_2$O (50 mL), taken up to pH=2 with HCl (10% aqueous solution) and extracted with CH$_2$Cl$_2$ (30 mL). The organic layer was dried over Na$_2$SO$_4$ (anhydrous), filtered and concentrated. Crude residue was purified by reverse phase chromatography (30 to 100% CH$_3$CN/H$_2$O) to give 88 mg of 2-(3,7-dimethyl-octa-2,6-dienyl)-3-hydroxy-5-pentyl-6-pentylamino-[1,4]benzoquinone [purple-colored solid, yield: 64%].

$^1$H NMR (CDCl$_3$, 300 MHz) δ ppm: 6.38 (bs, 1H), 5.13 (t, J=7.1 Hz, 1H), 5.05 (t, J=6.0 Hz, 1H), 3.47 (q, J=6.6 Hz, 2H), 3.06 (d, J=7.1 Hz, 2H), 2.49 (m, 2H), 2.08-1.93 (m, 4H), 1.72 (s, 3H), 1.65 (s, 3H), 1.57 (s, 3H), 1.42-1.28 (m, 12H), 0.91 (m, 6H).

Preparation Compound V

6-(3,7-dimethyl-octa-2, 6-dienyl)-5-hydroxy-3-pentyl-2-isobutylamino [1,4]benzoquinone Scheme 8

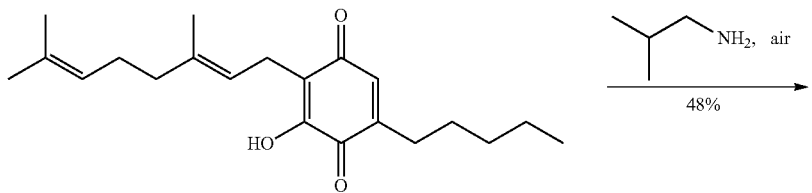

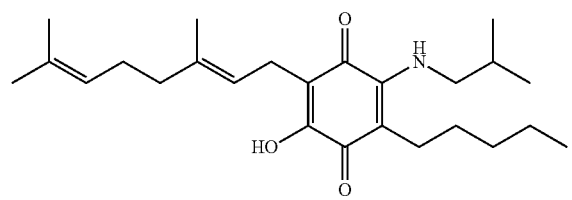

Isobutylamine (1.3 mL, 13.082 mmol) was added to a solution of compound CBQ-G (compound I) (101 mg, 0.306 mmol) in EtOH (10 mL). The reaction mixture was stirred at r.t. for 8 h (Scheme 8). It was poured into H₂O (50 mL), taken up to pH=2 with HCl (10% aqueous solution) and extracted with CH₂Cl₂ (30 mL). The organic layer was dried over Na₂SO₄ (anhydrous), filtered and concentrated. Crude residue was purified by reverse phase chromatography (30 to 100% CH₃CN/H₂O) to give 59 mg of 2-(3,7-dimethyl-octa-2,6-dienyl)-3-hydroxy-6-isobutylamino-5-pentyl-[1,4]benzoquinone [purple-colored solid, yield: 48%].

$^1$H NMR (CDCl$_3$, 250 MHz) δ ppm: 6.60 (bs, 1H), 5.11 (m, 2H), 3.28 (t, J=6.3 Hz, 2H), 3.06 (d, J=7.1 Hz, 2H), 2.49 (m, 2H), 2.07-1.84 (m, 4H), 1.72 (s, 3H), 1.65 (s, 3H), 1.57 (s, 3H), 1.41-1.27 (m, 7H), 1.02 (s, 3H), 0.98 (s, 3H), 0.89 (m, 3H).

Preparation Compound VI 6-(3,7-dimethyl-octa-2,6-dienyl)-5-hydroxy-3-pentyl-2-butylamino [1,4]benzoquinone Scheme 9

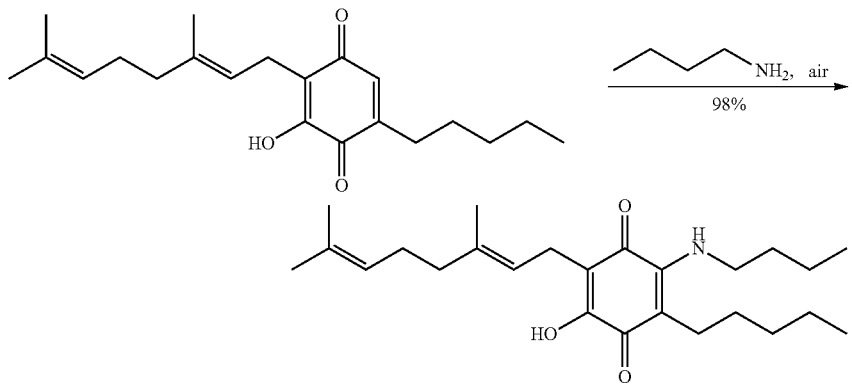

n-Butylamine (1.2 mL, 12.143 mmol) was added to a solution of compound CBG-Q (compound I) (102 mg, 0.309 mmol) in EtOH (12 mL). The reaction mixture was stirred at r.t. for 18 h (Scheme 9). It was poured into H₂O (50 mL), taken up to pH=2 with HCl (10% aqueous solution) and extracted with CH₂Cl₂ (30 mL). The organic layer was dried over Na₂SO₄ (anhydrous), filtered and concentrated to obtain 190 mg of 2-butylamino-6-(3,7-dimethyl-octa-2,6-dienyl)-5-hydroxy-3-pentyl-[1,4]benzoquinone [purple-colored solid, yield: 98%].

$^1$H NMR (CDCl$_3$, 250 MHz) δ ppm: 6.50 (bs, 1H), 5.09 (m, 2H), 3.47 (q, J=7.1 Hz, 2H), 3.05 (d, J=7.1 Hz, 2H), 2.48 (m, 2H), 2.08-1.90 (m, 4H), 1.72 (s, 3H), 1.64 (s, 3H), 1.57 (s, 3H), 1.50-1.22 (m, 10H), 1.00-0.84 (m, 6H).

Preparation Compound VII 6-(3,7-dimethyl-octa-2,6-dienyl)-5-hydroxy-3-pentyl-2-methylamino-[1,4]benzoquinone Scheme 10

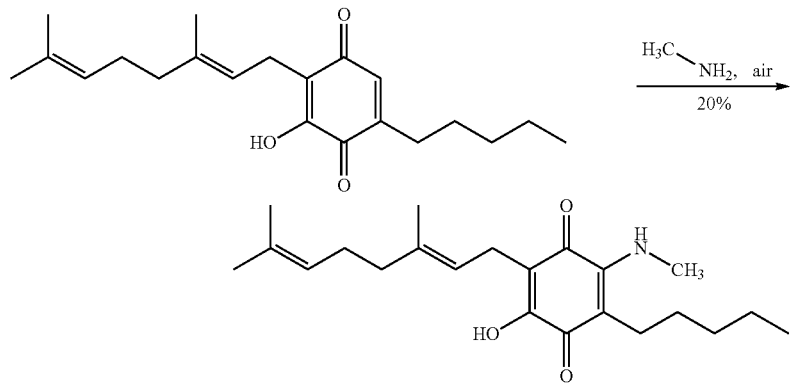

Methylamine (0.6 mL, 8 M solution in EtOH, 4.8 mmol) was added to a solution of compound CBG-Q (compound I) (102 mg, 0.309 mmol) in EtOH (10 mL). The reaction mixture was stirred at r.t. for 6 h (Scheme 10). It was poured into H$_2$O (50 mL), taken up to pH=2 with HCl (10% aqueous solution) and extracted with CH$_2$Cl$_2$ (30 mL). The organic layer was dried over Na$_2$SO$_4$ (anhydrous), filtered and concentrated. Crude residue was purified by reverse phase chromatography (30 to 100% CH$_3$CN/H$_2$O) to give 23 mg of 2-(3,7-dimethyl-octa-2,6-dienyl)-3-hydroxy-6-methylamino-5-pentyl-[1,4]benzoquinone [purple-colored solid, yield: 20%].

$^1$H NMR (CDCl$_3$, 300 MHz) δ ppm: 6.48 (bs, 1H), 5.12 (t, J=6.6 Hz, 1H), 5.06 (t, J=6.6 Hz, 1H), 3.20 (d, J=6.0 Hz, 3H), 3.06 (d, J=7.1 Hz, 2H), 2.55 (t, J=7.1 Hz, 2H), 2.07-1.92 (m, 4H), 1.72 (s, 3H), 1.65 (s, 3H), 1.57 (s, 3H), 1.49-1.23 (m, 6H), 0.89 (m, 3H).

Preparation Compound VIII 6-(3,7-imethyl-octa-2,6-dienyl)-5-hydroxy-3-pentyl-2-isopropylamino-[1,4]benzoquinone Scheme 11

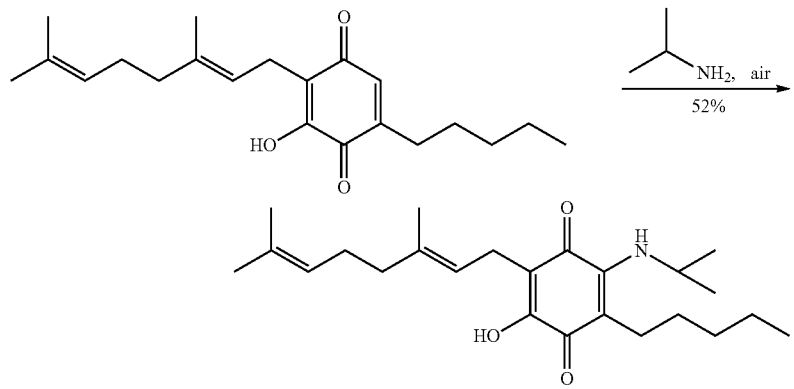

Isopropylamine (1.0 mL, 11.639 mmol) was added to a solution of compound CBG-Q (compound I) (101 mg, 0.306 mmol) in EtOH (10 mL). The reaction mixture was stirred at r.t. for 18 h (Scheme 11). It was poured into H$_2$O (50 mL), taken up to pH=2 with HCl (10% aqueous solution) and extracted with CH$_2$Cl$_2$ (30 mL). The organic layer was dried over Na$_2$SO$_4$ (anhydrous), filtered and concentrated. Crude residue was purified by reverse phase chromatography (30 to 100% CH$_3$CN/H$_2$O) to give 62 mg of 2-(3,7-dimethyl-octa-2,6-dienyl)-3-hydroxy-6-isopropylamino-5-pentyl-[1,4]benzoquinone [purple-colored solid, yield: 52%].

$^1$H NMR (CDCl$_3$, 300 MHz) δ ppm: 6.37 (s, 1H), 5.13 (t, J=6.6 Hz, 1H), 5.05 (t, J=6.6 Hz, 1H), 3.98 (m, 1H), 3.06 (d, J=7.1 Hz, 2H), 2.47 (m, 2H), 2.08-1.92 (m, 4H), 1.72 (s, 3H), 1.65 (s, 3H), 1.57 (s, 3H), 1.42-1.29 (m, 6H), 1.28 (s, 3H), 1.25 (s, 3H), 0.89 (m, 3H).

Preparation Compound IX 6-(3,7-dimethyl-octa-2,6-dienyl)-5-hydroxy-3-pentyl-2-b enzylamino [1,4]benzoquinone Scheme 12

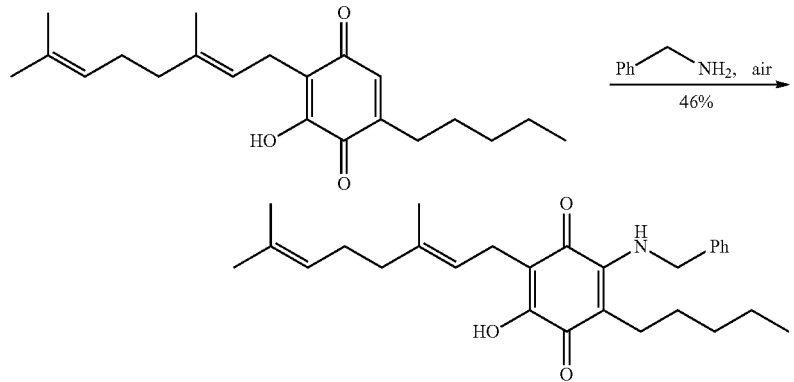

Benzylamine (1.3 mL, 11.913 mmol) was added to a solution of compound CBG-Q (compound I) (100 mg, 0.302 mmol) in EtOH (13 mL). The reaction mixture was stirred at r.t. for 18 h (Scheme 12). It was poured into H₂O (50 mL), taken up to pH=2 with HCl (10% aqueous solution) and extracted with CH₂Cl₂ (30 mL). The organic layer was dried over Na₂SO₄ (anhydrous), filtered and concentrated. Crude residue was purified by reverse phase chromatography (30 to 100% CH₃CN/H₂O) to give 61 mg of 2-benzylamino-6-(3,7-dimethyl-octa-2,6-dienyl)-5-hydroxy-3-pentyl-[1,4]benzoquinone [purple-colored solid, yield: 46%].

¹H NMR (CDCl₃, 300 MHz) δ ppm: 7.43-7.27 (m, 5H), 6.80 (bs, 1H), 5.18-5.02 (m, 2H), 4.67 (d, J=5.5 Hz, 2H), 3.07 (d, J=6.6 Hz, 2H), 2.47 (t, J=7.7 Hz, 2H), 2.09-1.92 (m, 4H), 1.72 (s, 3H), 1.65 (m, 3H), 1.57 (s, 3H), 1.47-1.24 (m, 6H), 0.88 (m, 3H).

Preparation Compound X 6-(3,7-dimethyl-octa-2,6-dienyl)-5-hydroxy-3-pentyl-2-(2,2-dimethyl-propylamino)-[1,4]benzoquinone Scheme 13

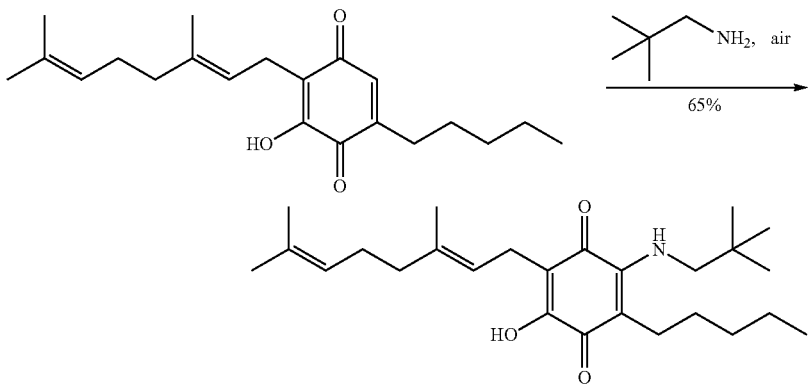

Neopentylamine (1.4 mL, 12.063 mmol) was added to a solution of compound CBG-Q (compound I) (100 mg, 0.303 mmol) in EtOH (14 mL). The reaction mixture was stirred at r.t. for 18 h (Scheme 13). It was poured into H₂O (50 mL), taken up to pH=2 with HCl (10% aqueous solution) and extracted with CH₂Cl₂ (30 mL). The organic layer was dried over Na₂SO₄ (anhydrous), filtered and concentrated. Crude residue was purified by reverse phase chromatography (30 to 100% CH₃CN/H₂O) to give 72 mg of 2-(3,7-dimethyl-octa-2,6-dienyl)-6-(2,2-dimethyl-propylamino)-3-hydroxy-5-pentyl [1,4]benzoquinone [purple-colored solid, yield: 65%].

¹H NMR (CDCl₃, 300 MHz) δ ppm: 6.62 (s, 1H), 5.14 (t, J=6.6 Hz, 1H), 5.05 (t, J=6.6 Hz, 1H), 3.27 (d, J=6.0 Hz, 2H), 3.07 (d, J=7.1 Hz, 2H), 2.50 (t, J=7.1 Hz, 2H), 2.09-1.92 (m, 4H), 1.72 (s, 3H), 1.65 (s, 3H), 1.57 (s, 3H), 1.47-1.25 (m, 6H), 1.02 (s, 9H), 0.90 (t, J=6.6 Hz, 3H).

Preparation Compound XI 6-(3,7-dimethyl-octa-2,6-dienyl)-5-hydroxy-3-pentyl-2-(3-methyl-butylamino)-[1,4]benzoquinone Scheme 14

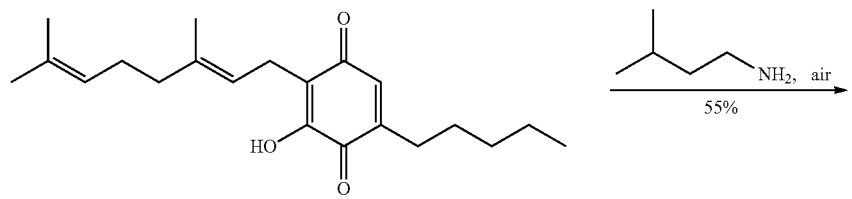

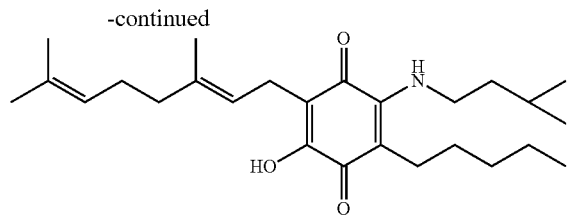

Isopentylamine (1.4 mL, 11.886 mmol) was added to a solution of compound CBG-Q (compound I) (100 mg, 0.303 mmol) in EtOH (14 mL). The reaction mixture was stirred at r.t. for 18 h (Scheme 14). It was poured into $H_2O$ (50 mL), taken up to pH=2 with HCl (10% aqueous solution) and extracted with $CH_2Cl_2$ (30 mL). The organic layer was dried over $Na_2SO_4$ (anhydrous), filtered and concentrated. Crude residue was purified by reverse phase chromatography (30 to 100% $CH_3CN/H_2O$) to give 40 mg of 2-(3,7-dimethyl-octa-2,6-dienyl)-3-hydroxy-6-(3-methyl-butylamino)-5-pentyl-[1,4]benzoquinone [purple-colored solid, yield: 55%].

$^1$H NMR (CDCl$_3$, 300 MHz) δ ppm: 6.38 (bs, 1H), 5.09 (m, 2H), 3.50 (q, J=6.0 Hz, 2H), 3.06 (d, J=7.1 Hz, 2H), 2.51 (t, J=7.1 Hz, 2H), 2.11-1.92 (m, 4H), 1.72 (s, 3H), 1.65 (s, 3H), 1.57 (s, 3H), 1.48-1.24 (m, 7H), 0.96 (s, 3H), 0.94 (s, 3H), 0.89 (m, 3H).

In Vitro Assays

Example 2. PPARg Agonistic Activity

To investigate the biological activities of the novel compounds we performed PPARg transactivation assays in HEK-293 cells and human primary fibroblasts cells.

HEK293T cells and human primary fibroblasts cells were maintained at 37° C. in a humidified atmosphere containing 5% $CO_2$ in DMEM supplemented with 10% fetal calf serum (FBS), and 1% (v/v) penicillin/streptomycin. Rosiglitazone was purchased from Cayman Chemical Company (Ann Arbor, Mich., USA). All other reagents were from Sigma Co (St Louis, Mo., USA). HEK293T cells ($2\times10^3$/well) (FIG. 1) or Human Dermal primary fibroblasts ($5\times10^3$/well) (FIG. 2) were seeded in BD Falcon™ White with Clear Bottom 96-well Microtest™ Optilux™ Plate for 24 hours. Afterwards, cells were transiently co-transfected with the expression vector GAL4-PPARγ and the luciferase reporter vector GAL4-luc using Roti©-Fect (Carl Roth, Karlsruhe, Germany) following the manufacturer's instructions. Twenty-four h post-transfection, cells were pretreated with increasing doses of the compounds for 6 hours. Then, the cells were lysed in 25 mM Tris-phosphate pH 7.8, 8 mM $MgCl_2$, 1 mM DTT, 1% Triton X-100, and 7% glycerol. Luciferase activity was measured in the cell lysate using a TriStar LB 941 multimode microplate reader (Berthold) and following the instructions of the Luciferase Assay Kit (Promega, Madison, Wis., USA). Protein concentration was measured by the Bradford assay (Bio-Rad, Richmond, Calif., USA). The background obtained with the lysis buffer was subtracted in each experimental value and the specific transactivation expressed as a fold induction over untreated cells. All the experiments were repeated at least three times. The plasmids used were Gal4-hPPARgamma (plasmid name: pCMV-BD-hPPARg, made in Sinal Laboratory, Dept. of Pharmacology, Dalhousie University) and Gal4 luc reporter plasmid that includes five Gal4 DNA binding sites fused to the luciferase gene. The above assay is illustrated by FIG. 1 and FIG. 2 which shows the effect of CBG-Q (compound I) and derivatives on PPARg activity by means of a transactivation assay performed in cells transiently overexpressing PPARg in combination with a luciferase reporter gene (PPARg-GAL4/GAL4-LUC) and treated with the compounds for 6 hours. Data are given as means with deviation standard error bars of three replicates. A significant increase in luciferase activity was seen with quinone derivates as compared with untreated cells. This result confirms that compound II is significantly more potent than compound CBG-Q (compound I) to activate PPARg at the concentrations of 1 to 25 μM. Compounds III to XII increase PPARg transactivation in a concentration dependent manner, being III, IV, V and XII the most active compounds. In addition higher concentrations (25 and 50 μM) of these compounds are particularly potent to activate PPARg compared to CBG-Q (compound I). Rosiglitazone, a full PPARg agonist, increased more than 100 times the activity of PPARg at the concentration of 1 μM. In contrast the maximal induction of PPARg activity induced by 1 μM concentration of the compounds described in the present invention was never higher than 12 times (i.e. compound II) indicating that these novel compounds are PPARg modulator and not PPARg full agonists.

Example 3. Cytotoxicity Assays

Electrophilic quinones induce cytotoxicity and activate the Nrf2 pathway, a cellular sensor of reactive oxygen species generation. In FIG. 3 it is analyzed the induced cell death in three different types of cells (N2a, HT22 and MO3.13) by compounds CBG-Q (compound I) and compounds (II) to (XII).

Three cell lines, MO3.13, N2A and HT22 cells were maintained at 37° C. in a humidified atmosphere containing 5% $CO_2$ in DMEM supplemented with 10% fetal calf serum (FBS), and 1% (v/v) penicillin/streptomycin. N2A, HT22 and MO3.13 cell viability was determined by the MTT assay. Briefly, cells were seeded at a density of $10^4$ cells/well in 96-well plates, 200 μl cell suspension per well, and cultured for 24 hours. Cells were then incubated with several concentrations of the compounds for 24 hours. After that, 100 μl of MTT (5 mg/ml) from a mixture solution of MTT: DMEM (1:2) was added to each well, and cells were incubated for 4 h at 37° C. in darkness. Then the reaction was stopped, supernatant removed and 100 μl of DMSO added to each well and incubated for 10 minutes in gentle shaking. Finally the absorbance was measured at 550 nm using a TriStar LB 941 (Berthold Technologies, GmbH & Co. KG). Control cells were set as 100% and data were referred to that value. The cell lines N2a (FIG. 3A), HT22 (FIG. 3B) and MO3.13 (FIG. 3C) cells were incubated for 24 h with the indicated doses of compounds CBG-Q (compound I) and compounds (II) to (XII), and cell viability was quantified by MTT assay. Results are shown as mean±S.D. from at least three independent experiments, and expressed as percentage of cell viability against the control sample (−). Control was set as 100% and data were referred to that value.

The results demonstrate that the cytotoxic activity associated to CBG-Q (compound I) correlated with its ability to induce Nrf2 activation. In the same sense the lack of cytotoxic activity for compounds II to XII derivatives in position 2 of CBG-Q) described in the present invention, is correlated with their inability to activate Nrf2.

Example 4. Nrf2 Transcriptional Activity

To study the activity of the compounds on the Nrf2 pathway we generated the HaCaT-ARE-Luc cell line. Nqo1 ARE-Luc reporter plasmid and pPGK-Puro plasmid were co-transfected into HaCat cells using Lipofectamine© 2000 transfection reagent (Life Technologies, Carlsbad, Ca, USA). Stable transformants were selected and maintained in RPMI 1640 containing 10% FBS, 1% penicillin-streptomycin and 10 µl/ml puromycin. HaCaT-ARE-Luc cells were incubated for 6 h with CBG-Q (compound I) and with compounds (II)-(VI) (A) or with compounds (VII)-(XII) (B) at the indicated concentrations, and protein lysates were prepared and analysed for luciferase activity as described in example 1. The prooxidant tert-Butylhydroquinone (tBHQ) at 20 µM was used as positive control. Fold activation level was calculated, taking the control sample (−) as reference (FIGS. 4A and 4B). Data are expressed as mean±S.D. from at least three independent experiments. The results ratify that the reactive electrophilic activity associated to CBG-Q (compound I) is missing in all the compounds (derivatives in position 2) described in the present invention.

Example 5. Neuroprotection Assays

Activation of the anti-inflammatory nuclear receptor PPARg plays an important role in neuroprotection and it is known that PPARg agonists prevent glutamate-induced cytotoxicity in neuronal cells.

Cultured N2A cells were pre-incubated with the compounds II, III, IV, V and XII at the indicated concentrations for 1 h and then treated with 5 mM glutamate to induce excitotoxicity during 24 h (FIG. 5). Cytotoxicity was determined by the MTT method as described in example 3. Results are shown as mean±S.D. from at least three independent experiments, and expressed as percentage of cell viability against the control sample (−). Control was set as 100% and data were referred to that value.

Those results show that compounds II, III, IV, V and XII, which are PPARg modulators, also protect neuronal cells from glutamate-induced apoptosis.

In Vivo Assays

Example 6. Induction of Experimental Autoimmune Encephalomyelitis (EAE)

PPARg modulators are of therapeutic use for neurodegenerative and inflammatory disorders and we have investigated the effects of two representative compounds of the present invention in three well-defined animal models of inflammation and neurodegeneration.

EAE was induced in female C57BL/6 mice at 6-8 weeks of age by subcutaneous immunization with myelin oligodendrocyte glycoprotein polypeptide ($MOG_{35-55}$) (300 µg) and 200 µg of *Mycobacterium tuberculosis* (H37Ra Difco, Franklin Lakes, N.J., USA) in a 1:1 mix with incomplete Freund's adjuvant (CFA, Sigma-Aldrich, Madrid, Spain). On the same day and 2 days later, mice were injected intraperitoneally (ip) with 200 ng of pertussis toxin (Sigma-Aldrich, Madrid, Spain) in 0.1 ml PBS. Control animals (CFA) were inoculated with the same emulsion without MOG and they did not receive pertussis toxin. Treatment started at day 6 post-immunization (p.i.) and consisted in daily injections of compounds III (FIG. 6) and XII (FIG. 8) at the indicated doses or of the vehicle alone (DMSO/PBS) for the following 21 days. The mice were examined daily for clinical signs of EAE and disease scores were measured as follows: 0, no disease; 1, limp tail; 2, limp tail and hind limb weakness; 3, hind limb paralysis; 4, hind limb and front limb paralysis; 5, moribund and death. All animals were sacrificed 28 days (p.i.) for further analysis. Once sacrificed, animals were dissected and their spinal cords were rapidly removed and quickly frozen in RNAlater (Sigma-Aldric, Germany).

It is shown in FIG. 6 that compound III clearly attenuated the clinical manifestations of Experimental Autoimmune Encephalomyelitis (EAE) induced by subcutaneous immunization with ($MOG_{35-55}$). Vehicle-treated mice developed a severe disease that peaked by day 16 post-injection (pi) reaching a score of 2.5 (maximal score is 3). In the mice that received compound III, the disease peaked on day 17 post-injection not reaching a score of 1.3 throughout the course of the experiment (day 6-day 28). The clinical symptoms in EAE correlated with the expression of the proinflammatory genes Ccl2, iNOs, TNFα, IFNg, IL-1b and IL-17 in the spinal cord of EAE mice that received the vehicle alone. By contrast, there was a significant decrease in all these parameters in the EAE mice that received compound III (FIG. 7). Moreover we show in FIG. 8 that compound XII also alleviated the clinical symptoms in EAE mice to the same extent than compound III confirming the anti-inflammatory activity of the compounds described in the present invention.

Example 7. Induction of Huntington's Disease (3NP Model)

The intoxication of mice with 3-Nitropropionic acid (3-NP), a potent irreversible inhibitor of mitochondrial complex II enzyme, leads to mitochondrial dysfunction and oxidative stress in animal models that results in a myriad of neurological, biochemical and histological effect that were reminiscent of some aspects of HD pathology. For example, 3NP-treated mice exhibited high scores in hindlimb clasping, dystonia, kyphosis and in the general locomotor activity compared to control animals.

Lesions of the striatum were induced with 3-NP in adult (16 week old; 30 g) male C57BL/6 mice (Harlan Ibérica, Barcelona, Spain). To this end, mice were subjected to seven intraperitoneal (i.p.) injections of 3NP (one injection each 12 hours) at a dose of 50 mg/kg (prepared in phosphate-buffered saline) for 3 days. These animals and their respective non-lesioned controls were used for pharmacological studies with compounds CBG-Q (compound I) and with compounds III and XII (FIG. 9). At least 6-8 animals were used per experimental group. Treatments consisted of four i.p. injections of the compounds at the indicated doses (one injection each 24 hours), or vehicle (DMSO 0.2%, BSA 5% in PBS) 30 min before the injections of 3NP. All animals were euthanized 12 hours after the last 3NP injection. Once euthanized, animals were dissected and their brains were rapidly removed. The right hemisphere was used to dissect the striatum, which was quickly frozen in RNAlater (Sigma-Aldrich, Germany) to analyzed inflammatory markers by Real Time PCR. The left hemisphere was fixed in fresh 4% paraformaldehyde (in 0.1M phosphate buffered-saline) for 48 hours at 4° C. and embedded in paraffin wax for histological analysis. Mice were subjected to behavioral tests for determining their neurological status. We evaluated the general locomotor activity, the hindlimb clasping and dystonia, and the truncal dystonia. All behavioral tests were conducted prior to drug injections to avoid acute effects of the compounds under investigation.

FIG. 9 shows that CBG-Q (compound I) was unable to prevent the clinical symptoms induced by 3-NP intoxication but compounds III and XII clearly alleviates such symptomatology.

We also used the striatal parenchyma of 3NP-lesioned mice for analysis of some histological and molecular markers related to inflammation and neurodegeneration, which are affected in this experimental model. The expression of inflammatory enzymes COX-2 and iNOs was significantly up regulated in 3NP-lesioned mice in parallel to increased expression of proinflammatory cytokines TNFα and IL-6. Compounds III (FIG. 10) and XII (FIG. 11) attenuated the up-regulation of pro-inflammatory markers COX-2, iNOS, TNFα and IL-6 in the striatum of mice treated with 3NP.

In FIG. 12 it is shown that the striatal parenchyma of these 3NP-lesioned animals showed an important degree of neuronal death that was confirmed by NeuN immunohistochemistry, which proved a reduction of more than 50% in the immunolabeling for this neuronal marker in the striatal parenchyma. The loss of neurons was accompanied by a notable decrease in GFAP$^+$ cells (astrogliosis) and an increased expression of Iba-1$^+$ cells (reactive microgliosis). Compound XII originated a preservation of striatal neurons against 3NP toxicity as revealed by NeuN staining. Moreover the treatment with Compound XII counteracted the lost of GFAP$^+$ cells induced by 3NP and prevented the induction of reactive microgliosis (Iba-1$^+$ cells).

Example 8. Induction of Parkinson's Disease (6-OHDA Model)

Compound III was also of therapeutic use in a murine model of Parkinson disease (PD).

C57BL/6 mice pretreated intracerebroventricularly (i.c.v.) were anesthetized with an intraperitoneal (i.p.) injection of 200 mg'kg of 2,2,2-tribromoethanol (Sigma-Aldrich) and placed in a stereotaxic frame with a mouse adapter (David Kopf Instruments, Tujunga, Calif., USA). Using a Hamilton syringe (Hamilton, Bonaduz, Switzerland), 4 µL of 6-OHDA-HBr solution (5 µg/µL) in 0.02% ascorbic acid (SigmaAldrich) were injected in the left striatum in two deposits at the following stereotaxic coordinates (mm from bregma): AP, +0.65; L, −2.0; V1, −4 and V2, −3.5, targeting the dorsolateral striatum. After the injection, the skin was sutured and the animals were removed from the stereotaxic instrument and placed on a heating pad for 30 min. The mice were subjected to chronic intraperitoneal treatment with compound III (10 mg/ml) or vehicle (14 days), starting 16 h after the 6-OHDA injection. Motor coordination was evaluated in the rotarod test (Ugo Basile, Rome, Italy) at crescent speed. Each day, mice had a 1 min training session in the immobile rod. If the mouse fell from the rotarod during the training session, it was placed back. Then the performance of the mice was tested in 5 min sessions every 20 min Thus, the speed of the rod was turned on up to 40 rpm for five minutes. The latency to fall off the rod was measured on consecutive days in lesioned mice following the compound III administration or vehicle control. Motor activity (ambulatory activity, mean velocity, resting time, fast movements and number of rearings) was evaluated using a computer-aided actimeter (FIG. 13).

The FIG. 13 shows that the appearance of motor symptoms that resemble human PD (changes in ambulatory activity, mean velocity, resting time, fast movement, number of rearing and rotarod performance) produced with 6-hydroxydopamine (6OHDA) were almost completely suppressed by the treatment with compound III.

Example 9. Histological Analysis (Example 7)

Brains from 3NP model were fixed in 4% paraformaldehyde and 5-µm-thick sections for immunohistochemical analysis of NeuN (FIG. 12A), a marker of neurons, GFAP (FIG. 12B), a marker of astrocytes and Iba-1 (FIG. 12C), a marker of microglial cells. For immunohistochemistry sections were incubated overnight at 4° C. with: (i) monoclonal anti-mouse NeuN antibody (Millipore, Mass., USA) used at $\frac{1}{100}$; (ii) monoclonal anti-mouse Iba-1 antibody (Millipore, Mass., USA) used at $\frac{1}{50}$, (iii) monoclonal anti-mouse GFAP antibody (Santa Cruz Biotechnology, Calif., USA) used at $\frac{1}{50}$. After incubation with the corresponding primary antibody, sections were washed in 0.1 M PBS and incubated O/N at 4° with Goat anti-mouse (Millipore, Mass., USA) secondary antibody. Reaction was revealed with diaminobenzidine. Negative control sections were obtained using the same protocol with omission of the primary antibody. All sections for each immunohistochemical procedure were processed at the same time and under the same conditions. A Leica DM2500 microscope and a Leica DFC 420C camera were used for slide observation and photography, and all image processing was done using ImageJ, the software developed and freely distributed by the US National Institutes of Health (Bethesda. Md., USA).

Example 10. Real-Time Quantitative PCR Used in the Invention (Examples 6 and 7)

Total RNA was isolated from striata (3NP model) or spinal cord (EAE model) using RNeasy Lipid Tissue Mini Kit (Qiagen, GmbH). The total amount of RNA extracted was quantitated by spectrometry at 260 nm and its purity from the ratio between the absorbance values at 260 and 280 nm. Genomic DNA was removed to eliminate DNA contamination. Single-stranded complementary DNA was synthesized from up to 1 µg of total RNA (pool from at least 3 animals per group) using iScript™ cDNA Synthesis Kit (Bio-Rad, Hercules, Calif., USA). The reaction mixture was kept frozen at −20° C. until enzymatic amplification. The iQ™ SYBR Green Supermix (Bio-Rad) was used to quantify mRNA levels for COX-2, TNF-α, IL-6, IL-17, IL-1β, IFN-γ, CCL-2 or iNOS depending on disease's model. Real-time PCR was performed using a CFX96 Real-Time PCR Detection System (Bio-Rad). The GAPDH housekeeping gene was used to standardize the mRNA expression levels in every sample. Expression levels were calculated using the $2^{-\Delta\Delta ct}$ method. Sequences of oligonucleotide primers are given in Table 2.

TABLE 2

List of mouse primer sequences used in quantitative Polymerase Chain Reaction.

| Genes | Forward | Reverse |
|---|---|---|
| IL-6 | 5'-GAACAACGATGATGCACTTGC-3' | 5'-TCCAGGTAGCTATGGTACTCC-3' |
| IL-1β | 5'-CTCCACCTCAATGGACAGAA-3' | 5'-GCCGTCTTTCATTACACAGG-3' |
| Ccl2 | 5'-GGGCCTGCTGTTCACAGTT-3' | 5'-CCAGCCTACTCATTGGGAT-3' |
| IFNγ | 5'-CTCAAGTGGCATAGATGTGGAAG-3' | 5'-GCTGGACCTGTGGGTTGTTGA-3' |
| IL-17 | 5'-CCTCAGACTACCTCAACCGTTC-3' | 5'-TTCATGTGGTGGTCCAGCTTTC-3' |
| iNOS | 5'-AACGGAGAACGTTGGATTTG-3' | 5'-CAGCACAAGGGGTTTTCTTC-3' |
| COX-2 | 5'-TGAGCAACTATTCCAAACCAGC-3 | 5'-GCACGTAGTCTTCGATCACTATC-3 |
| TNFα | 5'-AGAGGCACTCCCCCAAAAGA-3' | 5'-CGATCACCCCGAAGTTCCCATT-3' |
| GAPDH | 5'-TGGCAAAGTGGAGATTGTTGCC-3' | 5'-AAGATGGTGATGGGCTTCCCG-3' |

The present results substantiate the therapeutic use of the compounds described in the present inventions, particularly compounds II, III, IV, V and XII in neurodegenerative diseases and traumatic brain disorders where neuroinflammation and neurotoxicity play a significant role. In addition the compounds of the invention are particularly suitable as PPARg agonists particularly for treating inflammatory diseases (see Table 1 of the state of the art), metabolic diseases and type II diabetes.

REFERENCES

Ahmadian M, Suh J M, Hah N, Liddle C, Atkins A R, Downes M, Evans R M. PPARγ signaling and metabolism: the good, the bad and the future. 2013. Nat Med. 19:557-66
Barish G D, Narkar V A, Evans R M. 2006. PPARδ: a dagger in the heart of the metabolic syndrome. J Clin Invest. 116:590-597
Bernardo, A., Minghetti, L., 2008. Regulation of Glial Cell Functions by PPAR-gamma natural and Synthetic Agonists. PPAR Res. 2008, 864140.
Bolton J L, Trush M A, Penning T M, Dryhurst G, Monks T J. Role of quinones in toxicology. 2000. Chem Res Toxicol. 3:135-60.
Burstein S. 2005. PPAR-gamma: a nuclear receptor with affinity for cannabinoids. Life Sci. 77:1674-84.
Ciudin A, Hernandez C, Simó R. 2012. Update on cardiovascular safety of PPARgamma agonists and relevance to medicinal chemistry and clinical pharmacology. Curr Top Med Chem. 12: 585-604.
Doshi L S, Brahma M K, Bahirat U A, Dixit A V, Nemmani K V. 2012. Discovery and development of selective PPAR gamma modulators as safe and effective antidiabetic agents. Expert Opin Investig Drugs. 19:489-512.
Fievet C, Fruchart J C, Staels B, 2006. PPAR alpha and PPAR gamma dual agonists for the treatment of type2 diabetes and the metabolicsyndrome. Curr. Opin. Pharmacol. 6: 606-614.
Gelman, L., Feige, J. N., Desvergne, B., 2007. Molecular basis of selective PPARgamma modulation for the treatment of type 2 diabetes. Biochim. Biophys. Acta 1771: 1094-1107.
Granja A G, Carrillo-Salinas F, Pagani A, Gomez-Callas M, Negri R, Navarrete C, Mecha M, Mestre L, Fiebich B L, Cantarero I, Calzado M A, Bellido M L, Fernandez-Ruiz J, Appendino G, Guaza C, Muñoz E. 2012. A cannabigerol quinone alleviates neuroinflammation in a chronic model of multiple sclerosis. J Neuroimmune Pharmacol. 4:1002-16
Kostadinova R, Wahli W, Michalik L. 2005. PPARs in diseases: control mechanisms of inflammation. Curr Med Chem. 12: 2995-3009
Lehmann J M, Moore L B, Smith-Oliver T A, Wilkison W O, Willson T M, Kliewer S A. 1995. An antidiabetic thiazolidinedione is a high affinity ligand for peroxisome proliferator-activated receptor gamma (PPAR gamma). J Biol Chem. 270:12953-6.
Liu J, Li H, Burstein S H, Zurier R B, Chen J D, 2003. Activation and binding of peroxisome proliferator-activated receptor gamma by synthetic cannabinoid ajulemic acid. Mol. Pharmacol. 63: 983-992.
Monks T J, Jones D C. 2002. The metabolism and toxicity of quinones, quinonimines, quinone methides, and quinone-thioethers. Curr Drug Metab. 4:425-38.
Na H K, Surh Y J. 2013. Oncogenic potential of Nrf2 and its principal target protein heme oxygenase-1. Free Radic Biol Med. 67:353-365
O'Sullivan S E. 2007. Cannabinoids go nuclear: evidence for activation of peroxisome proliferator-activated receptors. Br J Pharmacol. 152:576-82.
Poulsen L, Siersbaek M, Mandrup S. PPARs: fatty acid sensors controlling metabolism. 2012. Semin Cell Dev Biol. 23:631-639.
Rosen E D, MacDougald O A. 2006. Adipocyte differentiation from the inside out. Nat Rev Mol Cell Biol. 7:885-96.
Singh, J. Petter, R. C. Baillie, T. A. Whitty, A. 2011. The resurgence of covalent drugs. Nat. Rev. Drug Discov. 10: 307-17
Solis L M, Behrens C, Dong W, Suraokar M, Ozburn N C, Moran C A, Corvalan A H, Biswal S, Swisher S G, Bekele B N, Minna J D, Stewart D J, Wistuba I I. 2010. Nrf2 and Keap1 abnormalities in non-small cell lung carcinoma and association with clinicopathologic features. Clin Cancer Res. 16:3743-53
M. B. Sporn, K. T. Liby. 2012. NRF2 and cancer: the good, the bad and the importance of context. Nat. Rev. Cancer. 12: 564-57
Stienstra R, Duval C, Muller M, Kersten S, 2007. PPARs, obesity, and inflammation. PPAR Res. 95974.

Sun Y, Bennett A. 2007. Cannabinoids: A New Group of Agonists of PPARs. PPAR Res. 23513.

Szeles, L., Torocsik, D., Nagy, L., 2007. PPARgamma in immunity and inflammation: cell types and diseases. Biochim. Biophys. Acta 1771: 1014-1030.

Tachibana K, Yamasaki D, Ishimoto K, Doi T. 2008. The Role of PPARs in Cancer. PPAR Res. 102737.

Tontonoz P, Spiegelman B M. 2008. Fat and beyond: the diverse biology of PPARgamma. Annu Rev Biochem. 77: 289-312.

Vanden Berghe W, Vermeulen L, Delerive P, DeBosscher K Staels B, Haegeman G. 2003. A paradigm for gene regulation: inflammation, NF-kB and PPAR. Adv. Exp. Med. Biol. 544:181-196.

Vivacell Biotechnology España, S. L. 2011. Cannabinoid quinone derivatives. WO 2011117429 A1.

The invention claimed is:

1. Compounds of Formula (I), or pharmaceutically acceptable salts thereof

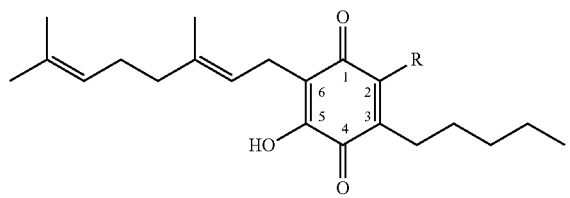
(I)

wherein R is the carbon atom of a group, represented by: aryl, linear or branched alkenyl, linear or branched alkynyl, or linear or branched alkoxycarbonyl groups; or wherein R is the nitrogen atom of a group, represented by: linear or branched alkylamino, arylamino, linear or branched alkenylamino, or linear or branched alkynylamino groups; or, alternatively, R represents a bond between 2 molecules of formula (I) forming a dimer.

2. Compound according to claim 1 selected from:

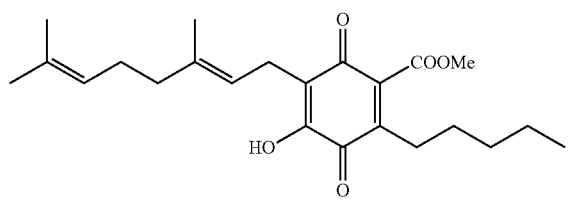
(II)

6-(3,7-dimethyl-octa-2,6-dienyl)-5-hydroxy-3-pentyl-2-methoxycarbonyl-[1,4]benzoquinone (II),

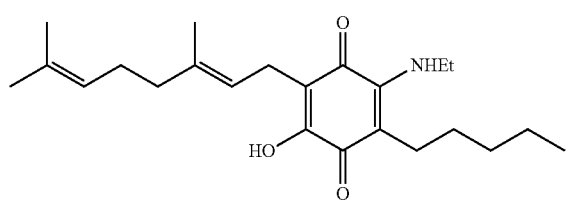
(III)

6-(3,7-dimethyl-octa-2,6-dienyl)-5-hydroxy-3-pentyl-2-ethylamino-[1,4]benzoquinone (III),

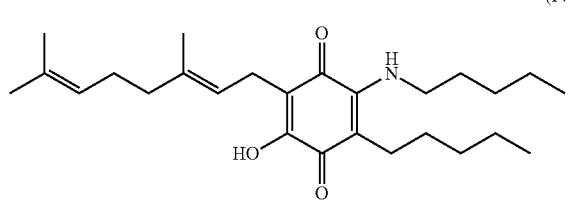
(IV)

6-(3,7-dimethyl-octa-2,6-dienyl)-5-hydroxy-3-pentyl-2-pentylamino-[1,4]benzoquinone (IV),

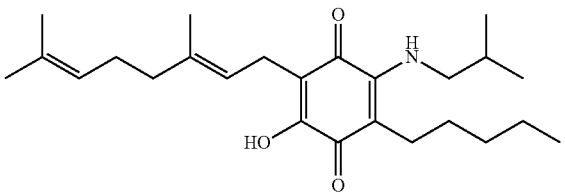
(V)

6-(3,7-dimethyl-octa-2, 6-dienyl)-5-hydroxy-3-pentyl-2-isobutylamino-[1,4]benzoquinone (V),

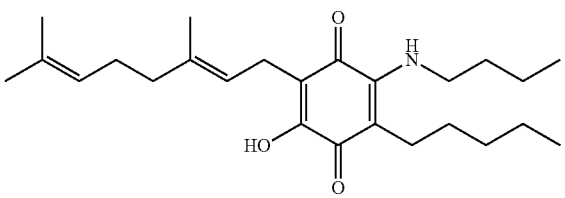
(VI)

6-(3,7-dimethyl-octa-2,6-dienyl)-5-hydroxy-3-pentyl-2-butylamino-[1,4]benzoquinone (VI),

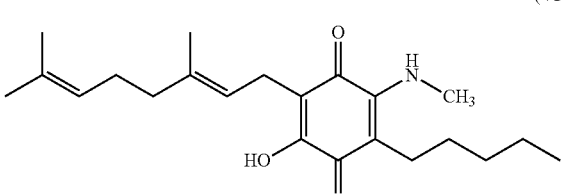
(VII)

6-(3,7-dimethyl-octa-2,6-dienyl)-5-hydroxy-3-pentyl-2-methylamino-[1,4]benzoquinone (VII),

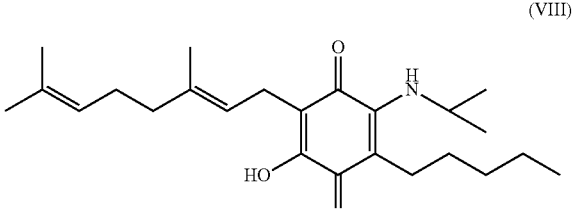
(VIII)

6-(3,7-dimethyl-octa-2,6-dienyl)-5-hydroxy-3-pentyl-2-isopropylamino-[1,4]benzoquinone (VIII),

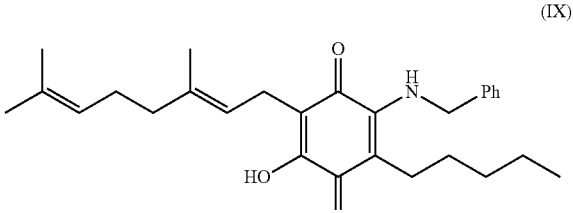
(IX)

6-(3,7-dimethyl-octa-2,6-dienyl)-5-hydroxy-3-pentyl-2-benzylamino-[1,4]benzoquinone (IX),

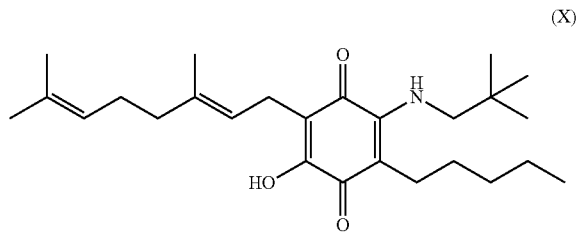 [SMILES: CCCCCC1=C(NCC(C)(C)C)C(=O)C(C/C=C(\C)CCC=C(C)C)=C(O)C1=O]

6-(3,7-dimethyl-octa-2,6-dienyl)-5-hydroxy-3-pentyl-2-(2,2-dimethyl-propylamino)-[1,4]benzoquinone (X),

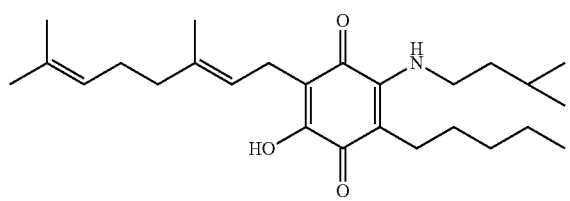

6-(3,7-dimethyl-octa-2,6-dienyl)-5-hydroxy-3-pentyl-2-(3-methyl-butylamino)-[1,4]benzoquinone (XI), and

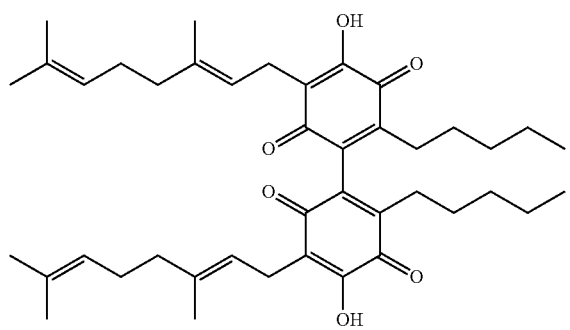

3,3'-bis((E)-3,7-dimethyl-octa-2,6-dienyl)-4,4'-dihydroxy-6,6'-dipentyl-1,1'-bi(cyclohexa-3,6-diene)-2,2',5,5'-tetraone (XII).

3. Compound according to claim 1 which is

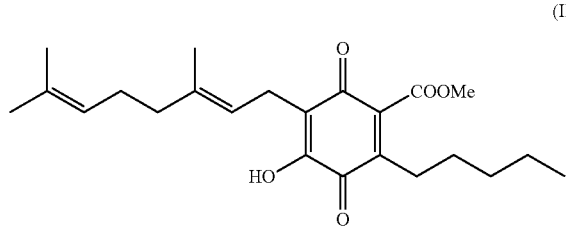

6-(3,7-dimethyl-octa-2,6-dienyl)-5-hydroxy-3-pentyl-2-methoxycarbonyl-[1,4]benzoquinone (II).

4. Compound according to claim 1 which is

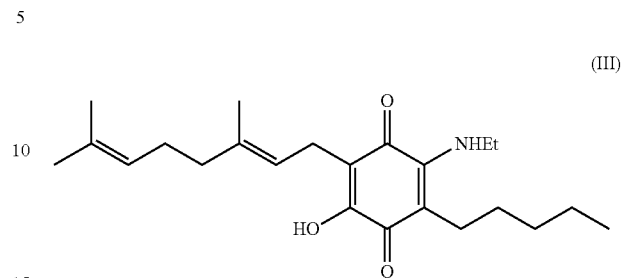

6-(3,7-dimethyl-octa-2,6-dienyl)-5-hydroxy-3-pentyl-2-ethylamino-[1,4]benzoquinone (III).

5. Compound according to claim 1 which is

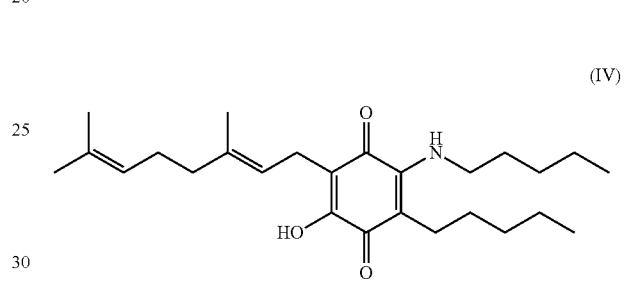

6-(3,7-dimethyl-octa-2,6-dienyl)-5-hydroxy-3-pentyl-2-pentylamino-[1,4]benzoquinone (IV).

6. Compound according to claim 1 which is

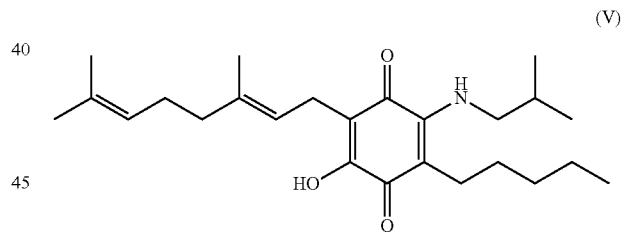

6-(3,7-dimethyl-octa-2, 6-dienyl)-5-hydroxy-3-pentyl-2-isobutylamino-[1,4]benzoquinone (V).

7. Compound according to claim 1 which is

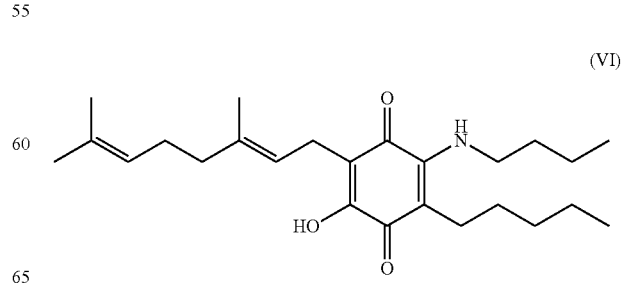

6-(3,7-dimethyl-octa-2,6-dienyl)-5-hydroxy-3-pentyl-2-butylamino-[1,4]benzoquinone (VI).

8. Compound according to claim 1 which is

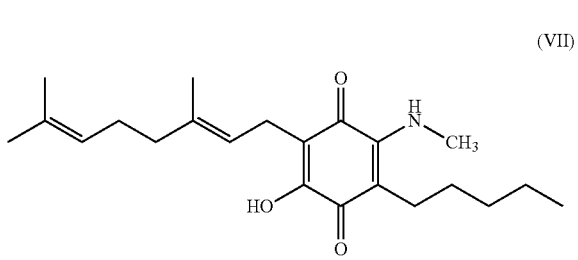 [SMILES: CCCCCC1=C(NC)C(=O)C(C/C=C(\C)CCC=C(C)C)=C(O)C1=O]

(VII)

6-(3,7-dimethyl-octa-2,6-dienyl)-5-hydroxy-3-pentyl-2-methylamino-[1,4]benzoquinone (VII).

9. Compound according to claim 1 which is

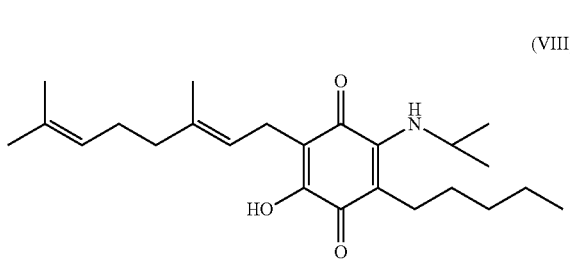

(VIII)

6-(3,7-dimethyl-octa-2,6-dienyl)-5-hydroxy-3-pentyl-2-isopropylamino-[1,4]benzoquinone (VIII).

10. Compound according to claim 1 which is

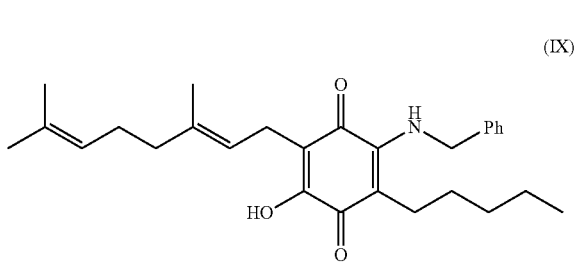 [SMILES: CCCCCC1=C(NCc2ccccc2)C(=O)C(C/C=C(\C)CCC=C(C)C)=C(O)C1=O]

(IX)

6-(3,7-dimethyl-octa-2,6-dienyl)-5-hydroxy-3-pentyl-2-benzylamino-[1,4]benzoquinone (IX).

11. Compound according to claim 1 which is

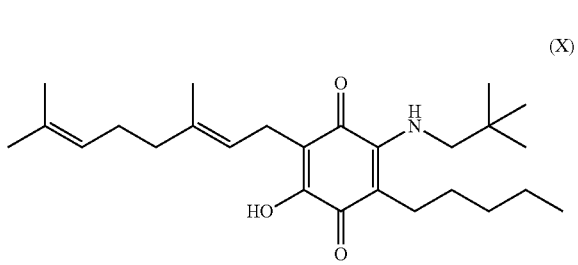 [SMILES: CCCCCC1=C(NCC(C)(C)C)C(=O)C(C/C=C(\C)CCC=C(C)C)=C(O)C1=O]

(X)

6-(3,7-dimethyl-octa-2,6-dienyl)-5-hydroxy-3-pentyl-2-(2,2-dimethyl-propylamino)-[1,4]benzoquinone (X).

12. Compound according to claim 1 which is

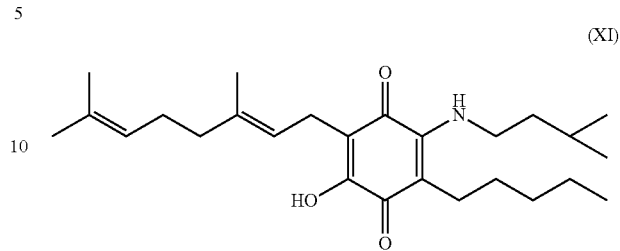

(XI)

6-(3,7-dimethyl-octa-2,6-dienyl)-5-hydroxy-3-pentyl-2-(3-methyl-butylamino)-[1,4]benzoquinone (XI).

13. Compound according to claim 1 which is

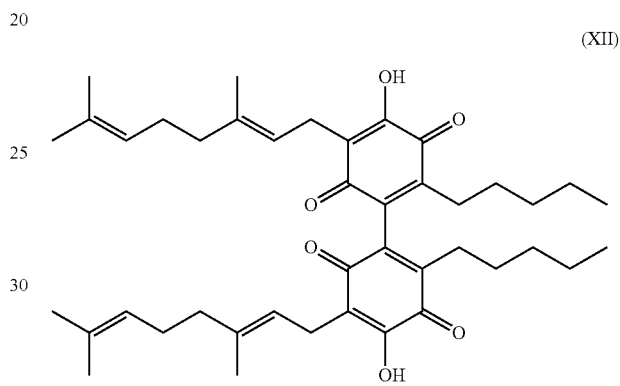

(XII)

3,3'-bis((E)-3,7-dimethyl-octa-2,6-dienyl)-4,4'-dihydroxy-6,6'-dipentyl-1,1'-bi(cyclohexa-3,6-diene)-2,2', 5,5'-tetraone (XII).

14. A composition comprising a compound of claim 1 or a pharmaceutically acceptable salt thereof, and at least one of a further active compound having additive or synergistic biological activity, a pharmaceutically inert ingredient, an excipient, or a carrier.

15. A method of treating a human or animal patient comprising administering an effective amount of a medicament comprising the compound of claim 1 or a pharmaceutically acceptable salt thereof to the patient sufficient to ameliorate the symptoms of a disease.

16. The method of claim 15, wherein the disease is a PPARg mediated disease.

17. The method of claim 16, wherein the PPARg mediated disease is selected from: atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, or type II diabetes.

18. The method of claim 15, wherein the medicament further comprises at least one of a further active compound having additive or synergistic biological activity, a pharmaceutically inert ingredient, an excipient, or a carrier.

\* \* \* \* \*

```
                            SEQUENCE LISTING

<160> NUMBER OF SEQ ID NOS: 18

<210> SEQ ID NO 1
   <211> LENGTH: 21
   <212> TYPE: DNA
   <213> ORGANISM: Artificial Sequence
   <220> FEATURE:
   <223> OTHER INFORMATION: Forward primer IL-6 mouse gene

<400> SEQUENCE: 1
gaacaacgat gatgcacttg c                                            21

<210> SEQ ID NO 2
   <211> LENGTH: 21
   <212> TYPE: DNA
   <213> ORGANISM: Artificial Sequence
   <220> FEATURE:
   <223> OTHER INFORMATION: Reverse primer IL-6 mouse gene

<400> SEQUENCE: 2
tccaggtagc tatggtactc c                                            21

<210> SEQ ID NO 3
   <211> LENGTH: 20
   <212> TYPE: DNA
   <213> ORGANISM: Artificial Sequence
   <220> FEATURE:
   <223> OTHER INFORMATION: Forward primer IL-1beta mouse gene

<400> SEQUENCE: 3
ctccacctca atggacagaa                                              20

<210> SEQ ID NO 4
   <211> LENGTH: 20
   <212> TYPE: DNA
   <213> ORGANISM: Artificial Sequence
   <220> FEATURE:
   <223> OTHER INFORMATION: Reverse primer IL-1beta mouse gene

<400> SEQUENCE: 4
gccgtctttc attacacagg                                              20

<210> SEQ ID NO 5
   <211> LENGTH: 19
   <212> TYPE: DNA
   <213> ORGANISM: Artificial Sequence
   <220> FEATURE:
   <223> OTHER INFORMATION: Forward primer Ccl2 mouse gene

<400> SEQUENCE: 5
gggcctgctg ttcacagtt                                               19

<210> SEQ ID NO 6
   <211> LENGTH: 19
   <212> TYPE: DNA
```

```
<213> ORGANISM: Artificial Sequence
<220> FEATURE:
<223> OTHER INFORMATION: Reverse primer Ccl2 mouse gene

<400> SEQUENCE: 6
ccagcctact cattgggat                                                  19

<210> SEQ ID NO 7
<211> LENGTH: 23
<212> TYPE: DNA
<213> ORGANISM: Artificial Sequence
<220> FEATURE:
<223> OTHER INFORMATION: Forward primer IFNgamma mouse gene

<400> SEQUENCE: 7
ctcaagtggc atagatgtgg aag                                             23

<210> SEQ ID NO 8
<211> LENGTH: 21
<212> TYPE: DNA
<213> ORGANISM: Artificial Sequence
<220> FEATURE:
<223> OTHER INFORMATION: Reverse primer IFNgamma mouse gene

<400> SEQUENCE: 8
gctggacctg tgggttgttg a                                               21

<210> SEQ ID NO 9
<211> LENGTH: 22
<212> TYPE: DNA
<213> ORGANISM: Artificial Sequence
<220> FEATURE:
<223> OTHER INFORMATION: Forward primer IL-17 mouse gene

<400> SEQUENCE: 9
cctcagacta cctcaaccgt tc                                              22

<210> SEQ ID NO 10
<211> LENGTH: 22
<212> TYPE: DNA
<213> ORGANISM: Artificial Sequence
<220> FEATURE:
<223> OTHER INFORMATION: Reverse primer IL-17 mouse gene

<400> SEQUENCE: 10
ttcatgtggt ggtccagctt tc                                              22

<210> SEQ ID NO 11
<211> LENGTH: 20
<212> TYPE: DNA
<213> ORGANISM: Artificial Sequence
<220> FEATURE:
<223> OTHER INFORMATION: Forward primer iNOS mouse gene

<400> SEQUENCE: 11
aacggagaac gttggatttg                                                 20

<210> SEQ ID NO 12
<211> LENGTH: 20
<212> TYPE: DNA
<213> ORGANISM: Artificial Sequence
<220> FEATURE:
<223> OTHER INFORMATION: Reverse primer iNOS mouse gene

<400> SEQUENCE: 12
cagcacaagg ggttttcttc                                                 20
```

```
<210> SEQ ID NO 13
<211> LENGTH: 22
<212> TYPE: DNA
<213> ORGANISM: Artificial Sequence
<220> FEATURE:
<223> OTHER INFORMATION: Forward primer COX-2 mouse gene

<400> SEQUENCE: 13
tgagcaacta ttccaaacca gc                                              22

<210> SEQ ID NO 14
<211> LENGTH: 23
<212> TYPE: DNA
<213> ORGANISM: Artificial Sequence
<220> FEATURE:
<223> OTHER INFORMATION: Reverse primer COX-2  mouse gene

<400> SEQUENCE: 14
gcacgtagtc ttcgatcact atc                                             23

<210> SEQ ID NO 15
<211> LENGTH: 20
<212> TYPE: DNA
<213> ORGANISM: Artificial Sequence
<220> FEATURE:
<223> OTHER INFORMATION: Forward primer TNFalpha mouse gene

<400> SEQUENCE: 15
agaggcactc ccccaaaaga                                                 20

<210> SEQ ID NO 16
<211> LENGTH: 22
<212> TYPE: DNA
<213> ORGANISM: Artificial Sequence
<220> FEATURE:
<223> OTHER INFORMATION: Reverse primer TNFalpha mouse gene

<400> SEQUENCE: 16
cgatcacccc gaagttccca tt                                              22

<210> SEQ ID NO 17
<211> LENGTH: 22
<212> TYPE: DNA
<213> ORGANISM: Artificial Sequence
<220> FEATURE:
<223> OTHER INFORMATION: Forward primer GAPDH mouse gene

<400> SEQUENCE: 17
tggcaaagtg gagattgttg cc                                              22

<210> SEQ ID NO 18
<211> LENGTH: 21
<212> TYPE: DNA
<213> ORGANISM: Artificial Sequence
<220> FEATURE:
<223> OTHER INFORMATION: Reverse primer GAPDH mouse gene

<400> SEQUENCE: 18
aagatggtga tgggcttccc g                                               21
```